US009999239B2

(12) United States Patent
Blotsky et al.

(10) Patent No.: US 9,999,239 B2
(45) Date of Patent: *Jun. 19, 2018

(54) METHODS AND COMPOSITIONS FOR ANIMAL FEED

(71) Applicant: CORE INTELLECTUAL PROPERTIES HOLDINGS, LLC, Goodyear, AZ (US)

(72) Inventors: Roger Blotsky, Goodyear, AZ (US); Walter H. Wilborn, Goodyear, AZ (US)

(73) Assignee: Core Intellectual Properties Holdings, LLC, Goodyear, AZ (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/388,356

(22) Filed: Dec. 22, 2016

(65) Prior Publication Data
US 2017/0202245 A1 Jul. 20, 2017

Related U.S. Application Data

(63) Continuation of application No. 14/790,798, filed on Jul. 2, 2015, now Pat. No. 9,549,565, which is a continuation of application No. 13/239,290, filed on Sep. 21, 2011, now Pat. No. 9,180,141.

(60) Provisional application No. 61/385,064, filed on Sep. 21, 2010.

(51) Int. Cl.
| *A61K 33/06* | (2006.01) |
| *A61K 33/42* | (2006.01) |
| *A61K 33/20* | (2006.01) |
| *A61K 33/32* | (2006.01) |
| *A61K 33/00* | (2006.01) |
| *A23K 50/75* | (2016.01) |
| *A23K 20/22* | (2016.01) |
| *A23K 20/20* | (2016.01) |
| *A23K 20/24* | (2016.01) |
| *A23K 20/26* | (2016.01) |

(52) U.S. Cl.
CPC .............. *A23K 50/75* (2016.05); *A23K 20/20* (2016.05); *A23K 20/22* (2016.05); *A23K 20/24* (2016.05); *A23K 20/26* (2016.05); *A23K 20/30* (2016.05); *A61K 33/00* (2013.01); *A61K 33/06* (2013.01); *A61K 33/20* (2013.01); *A61K 33/32* (2013.01); *A61K 33/42* (2013.01)

(58) Field of Classification Search
CPC .... A61K 2300/00; A61K 33/00; A61K 33/06; A61K 33/32; A61K 33/42; A61K 33/20; A61K 2236/00; A61K 2236/30; A61K 35/02; A61K 9/00; A23K 20/20; A23K 20/22; A23K 20/24; A23K 20/30; A23K 50/75; A23K 20/26
See application file for complete search history.

(56) References Cited

U.S. PATENT DOCUMENTS

| 3,092,111 | A | 6/1963 | Saperstein et al. |
| 3,553,313 | A | 1/1971 | Tort |
| 3,617,215 | A | 11/1971 | Sugahara et al. |
| 3,686,392 | A | 8/1972 | Hamada et al. |
| 3,990,885 | A | 11/1976 | Baillie et al. |
| 4,150,093 | A | 4/1979 | Kaminsky et al. |
| 4,163,800 | A | 8/1979 | Wickett |
| 4,299,826 | A | 11/1981 | Luedders |
| 4,533,459 | A | 8/1985 | Dente et al. |
| 4,610,883 | A | 9/1986 | Laurent et al. |
| 4,872,421 | A | 10/1989 | Laurent et al. |
| 4,904,627 | A | 2/1990 | Bhattacharyya |
| 4,976,971 | A | 12/1990 | Laurent et al. |
| 5,459,162 | A | 10/1995 | Saxton |
| 5,935,584 | A | 8/1999 | Guerrero et al. |
| 5,939,085 | A | 8/1999 | Jacobs et al. |
| 5,997,915 | A | 12/1999 | Bailey et al. |
| 6,042,839 | A | 3/2000 | Lahanas et al. |
| 6,294,179 | B1 | 9/2001 | Lee et al. |
| 6,316,041 | B1 | 11/2001 | Stock et al. |
| 6,432,430 | B1 | 8/2002 | Fitzjarrell |
| 6,764,991 | B2 | 7/2004 | Puvvada et al. |
| 7,074,565 | B2 | 7/2006 | Dunbar |
| 7,432,097 | B2 | 10/2008 | Short |
| 7,575,772 | B2 | 8/2009 | Shi et al. |
| 8,709,497 | B2 | 4/2014 | Blotsky et al. |
| 8,927,031 | B2 | 1/2015 | Blotsky et al. |
| 9,044,417 | B2 | 6/2015 | Blotsky et al. |

(Continued)

FOREIGN PATENT DOCUMENTS

| EP | 2207420 | 7/2010 |
| HK | 1146459 | 6/2011 |

(Continued)

OTHER PUBLICATIONS

Ames BN, Shigenaga MK, Hagen TM. (1993) Oxidants, antioxidants, and the degenerative diseases of aging. Proc Natl Acad Sci USA. 90(17): 7915-7922.
Anjos S, Polychronakos C. (2004) Mechanisms of genetic susceptibility to type I diabetes: beyond HLA. Mol. Gen. Metabolism, 81: 187-195.
Bahram et al. (2008) Genetics of type 2 diabetes mellitus and obesity—a review. Annals Medicine, 40: 2-10.
Batyuzhevskii et al., Energy, Protein, Mineral, and Vitamin Levels in the Nutrition of Breeding Roosters, Soversh. Korml. S-kh. Ptitsy, Ed. Smetnev, S.I., pp. 88-94 (reference found in STN) (1982).
Blando F, Gerardi C, Nicoletti I. (2004) Sour Cherry (*Prunus cerasus* L) Anthocyanins as Ingredients for Functional Foods. J Biomed Biotechnol. 2004(5): 253-258.

(Continued)

Primary Examiner — Mark V Stevens
(74) Attorney, Agent, or Firm — The Noblitt Group, PLLC

(57) ABSTRACT

The present invention is directed to methods and compositions that are useful in producing, feeding and growing animals. Compositions of the present invention comprise an extracted mineral element composition as disclosed herein. Animal lifespan and production is improved when provided with compositions comprising an extracted mineral element composition.

20 Claims, 14 Drawing Sheets

(56) References Cited

U.S. PATENT DOCUMENTS

| | | | |
|---|---|---|---|
| 9,107,869 | B2 | 8/2015 | Blotsky et al. |
| 9,180,141 | B1* | 11/2015 | Blotsky .......... A23K 20/30 |
| 9,549,565 | B2* | 1/2017 | Wilborn .......... A23K 20/30 |
| 2002/0069685 | A1 | 6/2002 | Adam |
| 2003/0049225 | A1 | 3/2003 | Rucker |
| 2003/0068359 | A1 | 4/2003 | Register |
| 2003/0108624 | A1 | 6/2003 | Kosbab |
| 2003/0224028 | A1 | 12/2003 | Galey |
| 2004/0081712 | A1 | 4/2004 | Hermansen |
| 2004/0161435 | A1 | 8/2004 | Gupta |
| 2004/0258597 | A1 | 12/2004 | Michalakos |
| 2006/0093685 | A1 | 5/2006 | Mower et al. |
| 2007/0031462 | A1 | 2/2007 | Blotsky et al. |
| 2007/0082106 | A1 | 4/2007 | Lee et al. |
| 2007/0116832 | A1 | 5/2007 | Prakash |
| 2007/0148186 | A1 | 6/2007 | Ketzis |
| 2007/0190173 | A1 | 8/2007 | Blotsky et al. |
| 2009/0226545 | A1 | 9/2009 | Blotsky et al. |
| 2010/0129465 | A1 | 5/2010 | Blotsky et al. |
| 2015/0250817 | A1 | 9/2015 | Blotsky et al. |

FOREIGN PATENT DOCUMENTS

| | | |
|---|---|---|
| JP | 2001294896 | 10/2001 |
| WO | WO 2007/149410 | 12/2007 |
| WO | WO 2009/023975 | 2/2009 |
| WO | WO 2009/049246 | 4/2009 |

OTHER PUBLICATIONS

Board of Agriculture (BOA), Nutrient Requirements of Poultry: Ninth Revised Edition (1994).

Dignan P. (1981) Teratogenic Risk and Counseling in Diabetes. Clin Obstet Gynecol., 24(1): 149-159.

Field LL. (2002) Genetic linkage and association studies of Type I diabetes: challenges and rewards. Diabetologia, 45 (1):21-35.

Greiner DL, Rossini AA, Mordes JP. (2001) Translating data from animal models into methods for preventing human autoimmune diabetes mellitus: caveat emptor and primum non nocere. Clin Immunol., 100(2): 134-143.

Ikegami H, Fujisawa T, Ogihara T. (2004) Mouse models of type 1 and type 2 diabetes derived from the same closed colony: genetic susceptibility shared between two types of diabetes. ILAR J., 45(3): 268-277.

Jafar-Mohammadi, B. et al., Genetics of Type 2 Diabetes Mellitus and Obesity: A Review, Annals Medicine, 40: 2-10 (2008).

Li F, Wang CN, Zhou Y, Xiong WW. (2006) Analysis of contents of copper and cadmium in Siraitia grosvenori. Welling Yuansu Yu Jiankang Yanjiu, 23(6): 30-34.

Ou B, Hampsch-Woodill M, Prior RL. (2001) Development and validation of an improved oxygen radical absorbance capacity assay using fluorescein as the fluorescent probe. J Agric Food Chem. 49(10): 4619-4626.

Product Description for Low-Carb Natural Sweetener made by TriMedica (retrieved from www.gnpd.com on Feb. 20, 2015).

Rahbar S, Figarola JL. (2002) Inhibitors and Breakers of Advanced Glycation (AGEs): A Review. Curr. Med. Chem.—Imun., Endoc. & Metab. Agents, 2: 135-161.

Rich, S.S. et al., Recent Progress in the Genetics of Diabetes, Horm Res, 71(Suppl): 17-23 (2009).

Schneideler, Trace Mineral Balance in Poultry, Zootecnica, Nutrition (Dec. 2008).

Simpson RW, Shaw JE, Zimmet PZ. (2003) The prevention of type 2 diabetes—lifestyle change or pharmacotherapy? A challenge for the 21st century. Diabetes Res Clin Pract., 59(3): 165-180.

Suzuki YA, Murata Y, Inui H, Sugiura M, Nakano Y. (2005) Triterpene glycosides of Siraitia grosvenori inhibit rat intestinal maltase and suppress the rise in blood glucose level after a single oral administration of maltose in rats. J Agric Food Chem., 53(8): 2941-2946.

Wicker LS, Moule CL, Fraser H, Penha-Goncalves C, Rainbow D, Garner VE, Chamberlain G, Hunter K, Howlett S, Clark J, Gonzalez-Munoz A, Cumiskey AM, Tiffen P, Howson J, Healy B, Smink LJ, Kingsnorth A, Lyons PA, Gregory S, Rogers J, Todd JA, Peterson LB. (2005) Natural genetic variants influencing type 1 diabetes in humans and in the NOD mouse. Novartis Found Symp., 267: 57-65.

Xiangyang Q, Weijun C, Liegang L, Ping Y, Bijun X. (2006) Effect of a Siraitia grosvenori extract containing mogrosides on the cellular immune system of type 1 diabetes mellitus mice. Mol Nutr Food Res. 50(8): 732-738.

International Search Report and Written Opinion dated Jun. 13, 2008 for PCT/US2007/014229, which was filed Jun. 19, 2007and published as WO 2007/149410 (Applicant—Blotsky et al.; Inventor—Blotsky et al.).

International Preliminary Report on Patentability and Written Opinion dated Jun. 19, 2007 for PCT/US2007/014229, which was filed Jun. 21, 2006 and published as WO 2007/149410 (Applicant—Blotsky et al.; Inventor—Blotsky et al.).

International Search Report dated Jan. 8, 2009 for PCT/US2008/079632, which was filed Oct. 10, 2008 and published as WO 2009/049246 (Applicant—Global Organics LLC; Inventor—Blotsky et al.).

International Preliminary Report on Patentability and Written Opinion dated Apr. 13, 2010 for PCT/US2008/079632, which was filed Oct. 10, 2008 and published as WO 2009/049246 (Applicant—Global Organics LLC; Inventor—Blotsky et al.).

Extended European Search Report dated Dec. 9, 2010 for EP Application Serial No. 08838086.0 which was filed Oct. 10, 2008 and published as EP 2207420 (Applicant—Global Organics LLC; Inventor—Blotsky et al.).

Restriction Requirement dated Apr. 12, 2007 for U.S. Appl. No. 10/725,729, filed Dec. 2, 2003 (Inventor—Blotsky et al.) (6 pages).

Response to Restriction Requirement dated May 31, 2007 for U.S. Appl. No. 10/725,729, filed Dec. 2, 2003 (Inventor—Blotsky et al.) (2 pages).

Non-Final Office Action dated Jun. 14, 2007 for U.S. Appl. No. 10/725,729, filed Dec. 2, 2003 (Inventor—Blotsky et al.) (10 pages).

Response to Non-Final Office Action dated Sep. 14, 2007 for U.S. Appl. No. 10/725,729, filed Dec. 2, 2003 (Inventor—Blotsky et al.) (7 pages).

Restriction Requirement dated Nov. 26, 2007 for U.S. Appl. No. 10/725,729, filed Dec. 2, 2003 (Inventor—Blotsky et al.) (5 pages).

Response to Restriction Requirement dated Jan. 28, 2008 for U.S. Appl. No. 10/725,729, filed Dec. 2, 3003 (Inventor—Blotsky et al.) (5 pages).

Final Office Action dated Apr. 30, 2008 for U.S. Appl. No. 10/725,729, filed Dec. 2, 2003 (Inventor—Blotsky et al.) (11 pages).

Response to Final Office Action dated Sep. 30, 2008 for U.S. Appl. No. 10/725,729, filed Dec. 2, 2003 (Inventor—Blotsky et al.) (11 pages).

Notice of Non-Compliant Amendment dated Jan. 9, 2009 for U.S. Appl. No. 10/725,729, filed Dec. 2, 2003 (Inventor—Blotsky et al.) (4 pages).

Response to Notice of Non-Compliant Amendment dated Jun. 23, 2009 for U.S. Appl. No. 10/725,729, filed Dec. 2, 2003 (Inventor—Blotsky et al.) (15 pages).

Examiner's Interview Summary dated Jul. 1, 2009 for U.S. Appl. No. 10/725,729, filed Dec. 2, 2003 (Inventor—Blotsky et al.) (4 pages).

Supplemental Response to Notice of Non-Compliant Amendment dated Jul. 8, 2009 for U.S. Appl. No. 10/725,729, filed Dec. 2, 2003 (Inventor—Blotsky et al.) (12 pages).

Non-Final Office Action dated Sep. 29, 2009 for U.S. Appl. No. 10/725,729, filed Dec. 2, 2003 (Inventor—Blotsky et al.) (11 pages).

Response to Non-Final Office Action dated Mar. 29, 2010 for U.S. Appl. No. 10/725,729, filed Dec. 2, 2003 (Inventor—Blotsky et al.) (13 pages).

Examiner's Interview Summary dated May 25, 2010 for U.S. Appl. No. 10/725,729, filed Dec. 2, 2003 (Inventor—Blotsky et al.) (4 pages).

(56) References Cited

OTHER PUBLICATIONS

Final Office Action dated Jun. 24, 2010 for U.S. Appl. No. 10/725,729, filed Dec. 2, 2003 (Inventor—Blotsky et al.) (11 pages).
Applicant's Response to Interview Summary dated Jun. 25, 2010 for U.S. Appl. No. 10/725,729, filed Dec. 2, 2003 (Inventor—Blotsky et al.) (2 pages).
Response to Final Office Action dated Sep. 24, 2010 for U.S. Appl. No. 10/725,729, filed Dec. 2, 2003 (Inventor—Blotsky et al.) (14 pages).
Non-Final Office Action dated Feb. 21, 2013 for U.S. Appl. No. 10/725,729, filed Dec. 2, 2003 (Inventor—Blotsky et al.) (12 pages).
Response to Non-Final Office Action dated May 21, 2013 for U.S. Appl. No. 10/725,729, filed Dec. 2, 2003 (Inventor—Blotsky et al.) (9 pages).
Final Office Action dated Sep. 11, 2013 for U.S. Appl. No. 10/725,729, filed Dec. 2, 2003 (Inventor—Blotsky et al.) (8 pages).
Applicant-Initiated Interview Summary dated Oct. 22, 2013 for U.S. Appl. No. 10/725,729, filed Dec. 2, 2003 (Inventor—Blotsky et al.) (3 pages).
Response to Final Office Action dated Nov. 8, 2013 for U.S. Appl. No. 10/725,729, filed Dec. 2, 2003 (Inventor—Blotsky et al.) (8 pages).
Notice of Allowance dated Dec. 2, 2013 for U.S. Appl. No. 10/725,729, filed Dec. 2, 2003 (Inventor—Blotsky et al.) (11 pages).
Supplemental Notice of Allowance dated Mar. 31, 2014 for U.S. Appl. No. 10/725,729, filed Dec. 2, 2003 (Inventor—Blotsky et al.) (2 pages).
Issue Notification dated Apr. 9, 2014 for U.S. Appl. No. 10/725,729, filed Dec. 2, 2003 (Inventor—Blotsky et al.) (1 page).
Restriction Requirements dated Mar. 8, 2007 for U.S. Appl. No. 11/472,536, filed Jun. 21, 2006 (Inventor—Blotsky et al.).
Response to Restriction Requirement dated May 14, 2007 for U.S. Appl. No. 11/472,536, filed Jun. 21, 2006 (Inventor—Blotsky et al.).
Non-Final Office Action dated Jun. 15, 2007 for U.S. Appl. No. 11/472,536, filed Jun. 21, 2006 (Inventor—Blotsky et al.).
Response after Non-Final Action dated Sep. 17, 2007 for U.S. Appl. No. 11/472,536, filed Jun. 21, 2006 (Inventor—Blotsky et al.).
Final Office Action dated Nov. 26, 2007 for U.S. Appl. No. 11/472,536, filed Jun. 26, 2006 (Inventor—Blotsky et al.).
Amendment after Final Office Action dated Jan. 28, 2008 for U.S. Appl. No. 11/472,536, filed Jun. 21, 2006 (Inventor—Blotsky et al.).
Advisory Action dated Feb. 13, 2008 for U.S. Appl. No. 11/472,536, filed Jun. 21, 2006 (Inventor—Blotsky et al.).
Response after Final Action with Request for Continued Examination dated Mar. 28, 2008 for U.S. Appl. No. 11/472,536, filed Jun. 21, 2006 (Inventor—Blotsky et al.).
Restriction Requirements dated Jun. 20, 2008 for U.S. Appl. No. 11/472,536, filed Jun. 21, 2006 (Inventor—Blotsky et al.).
Response to Restriction Requirement dated Nov. 20, 2008 for U.S. Appl. No. 11/472,536, filed Jun. 21, 2006 (Inventor—Blotsky et al.).
Non-Final Office Action dated Feb. 5, 2009 for U.S. Appl. No. 11/472,536, filed Jun. 21, 2006 (Inventor—Blotsky et al.).
Response after Non-Final Action dated Jul. 6, 2009 for U.S. Appl. No. 11/472,536, filed Jun. 21, 2006 (Inventor—Blotsky et al.).
Final Office Action dated Oct. 9, 2009 for U.S. Appl. No. 11/472,536, filed Jun. 21, 2006 (Inventor—Blotsky et al.).
Response after Final Action with Request for Continued Examination dated Feb. 9, 2010 for U.S. Appl. No. 11/472,536, filed Jun. 21, 2006 (Inventor—Blotsky et al.).
Non-Final Office Action dated Feb. 19, 2010 for U.S. Appl. No. 11/472,536, filed Jun. 21, 2006 (Inventor—Blotsky et al.).
Examiner Interview Summary dated May 25, 2010 for U.S. Appl. No. 11/472,536, filed Jun. 21, 2006 (Inventor—Blotsky et al.).
Response to Interview Summary dated Jun. 25, 2010 for U.S. Appl. No. 11/472,536, filed Jun. 21, 2006 (Inventor—Blotsky et al.).
Response after Non-Final Action dated Jul. 19, 2010 for U.S. Appl. No. 11/472,536, filed Jun. 21, 2006 (Inventor—Blotsky et al.).
Non-Final Office Action dated Oct. 27, 2010 for U.S. Appl. No. 11/472,536, filed Jun. 21, 2006 (Inventor—Blotsky et al.).
Response to Non-Final Office Action dated Mar. 28, 2011 for U.S. Appl. No. 11/472,536, filed Jun. 21, 2006 (Inventor—Blotsky et al.) (16 pages).
Final Office Action dated Jun. 8, 2011 for U.S. Appl. No. 11/472,536, filed Jun. 21, 2006 (Inventor—Blotsky et al.) (15 pages).
Response to Final Office Action dated Nov. 8, 2011 for U.S. Appl. No. 11/472,536, filed Jun. 21, 2006 (Inventor—Blotsky et al.) (12 pages).
Summary of Examiner Interview dated Dec. 5, 2013 for U.S. Appl. No. 11/472,536, filed Jun. 21, 2006 (Inventor—Blotsky et al.) (2 pages).
Non-Final Office Action dated Dec. 17, 2013 for U.S. Appl. No. 11/472,536, filed Jun. 21, 2006 (Inventor—Blotsky et al.) (12 pages).
Notice of Abandonment dated Jul. 3, 2014 for U.S. Appl. No. 11/472,536, filed Jun. 21, 2006 (Inventor—Blotsky et al.) (2 pages).
Non-Final Office Action dated Oct. 4, 2007 for U.S. Appl. No. 11/638,311, filed Dec. 12, 2006 (Inventor—Blotsky et al.).
Response after Non-Final Action dated Feb. 4, 2008 for U.S. Appl. No. 11/638,311, filed Dec. 12, 2006 (Inventor—Blotsky et al.).
Restriction Requirement dated Apr. 29, 2008 for U.S. Appl. No. 11/638,311, filed Dec. 12, 2006 (Inventor—Blotsky et al.).
Response to Restriction Requirement dated May 29, 2008 for U.S. Appl. No. 11/638,311, filed Dec. 12, 2006 (Inventor—Blotsky et al.).
Notice of Information or Non-Responsive Amendment dated Jul. 28, 2008 for U.S. Appl. No. 11/638,311, filed Dec. 12, 2006 (Inventor—Blotsky et al.).
Response to Restriction Requirement dated Aug. 1, 2008 for U.S. Appl. No. 11/638,311, filed Dec. 12, 2006 (Inventor—Blotsky et al.).
Final Office Action dated Oct. 20, 2008 for U.S. Appl. No. 11/638,311, filed Dec. 12, 2006 (Inventor—Blotsky et al.).
Response after Final Action with Request for Continued Examination dated Apr. 20, 2009 for U.S. Appl. No. 11/638,311, filed Dec. 12, 2006 (Inventor—Blotsky et al.).
Non-Final Office Action dated Jun. 19, 2009 for U.S. Appl. No. 11/638,311, filed Dec. 12, 2006 (Inventor—Blotsky et al.).
Response after Non-Final Action dated Dec. 21, 2009 for U.S. Appl. No. 11/638,311, filed Dec. 12, 2006 (Inventor—Blotsky et al.).
Final Office Action dated Mar. 31, 2010 for U.S. Appl. No. 11/638,311, filed Dec. 12, 2006 (Inventor—Blotsky et al.).
Examiner Interview Summary dated May 28, 2010 for U.S. Appl. No. 11/638,311, filed Dec. 12, 2006 (Inventor—Blotsky et al.).
Response to Interview Summary dated Jun. 25, 2010 for U.S. Appl. No. 11/638,311, filed Dec. 12, 2006 (Inventor—Blotsky et al.).
Response after Final Action with Request for Continued Examination dated Jul. 30, 2010 for U.S. Appl. No. 11/638,311, filed Dec. 12, 2006 (Inventor—Blotsky et al.).
Non-Final Office Action dated Oct. 27, 2010 for U.S. Appl. No. 11/638,311, filed Dec. 12, 2006 (Inventor—Blotsky et al.).
Response to Non-Final Office Action dated Mar. 28, 2011 for U.S. Appl. No. 11/638,311, filed Dec. 12, 2006 (Inventor—Blotsky et al.) (15 pages).
Final Office Action dated Jun. 8, 2011 for U.S. Appl. No. 11/638,311, filed Dec. 12, 2006 (Inventor—Blotsky et al.) (16 pages).
Response to Final Office Action dated Nov. 8, 2011 for U.S. Appl. No. 11/638,311, filed Dec. 12, 2006 (Inventor—Blotsky et al.) (13 pages).
Summary of Examiner Interview dated Dec. 5, 2013 for U.S. Appl. No. 11/638,311, filed Dec. 12, 2006 (Inventor—Blotsky et al.) (2 pages).
Non-Final Office Action dated Dec. 16, 2013 for U.S. Appl. No. 11/638,311, filed Dec. 12, 2006 (Inventor—Blotsky et al.) (13 pages).
Notice of Abandonment dated Jul. 2, 2014 for U.S. Appl. No. 11/638,311, filed Dec. 12, 2006 (Inventor—Blotsky et al.) (2 pages).

(56) References Cited

OTHER PUBLICATIONS

Preliminary Amendment dated Mar. 28, 2014 for U.S. Appl. No. 14/229,340, filed Mar. 28, 2014 now U.S. Pat. No. 9,044,417 on Jun. 2, 2015 (Inventor—Blotsky et al.) (4 pages).
Non-Final Office Action dated Aug. 28, 2014 for U.S. Appl. No. 14/229,340, filed Mar. 28, 2014 now U.S. Pat. No. 9,044,417 on Jun. 2, 2015 (Inventor—Blotsky et al.) (11 pages).
Response to Non-Final Office Action dated Nov. 26, 2014 for U.S. Appl. No. 14/229,340, filed Mar. 28, 2014 now U.S. Pat. No. 9,044,417 on Jun. 2, 2015 (Inventor—Blotsky et al.) (8 pages).
Supplemental Response dated Jan. 8, 2015 for U.S. Appl. No. 14/229,340, filed Mar. 28, 2014 now U.S. Pat. No. 9,044,417 on Jun. 2, 2015 (Inventor—Blotsky et al.) (6 pages).
Notice of Allowance dated Jan. 27, 2015 for U.S. Appl. No. 14/229,340, filed Mar. 28, 2014 now U.S. Pat. No. 9,044,417 on Jun. 2, 2015 (Inventor—Blotsky et al.) (8 pages).
Issue Notification dated Jun. 2, 2015 for U.S. Appl. No. 14/229,340, filed Mar. 28, 2014 now U.S. Pat. No. 9,044,417 on Jun. 2, 2015 (Inventor—Blotsky et al.) (1 page).
Preliminary Amendment dated May 20, 2015 for U.S. Appl. No. 14/717,660, filed May 20, 2015 and published as US 2015/0250817 on Sep. 10, 2015 (Inventor—Blotsky et al.) (4 pages).
Non-Final Office Action dated May 18, 2015 for U.S. Appl. No. 14/717,660, filed May 20, 2015 and published as US 2015/0250817 on Sep. 10, 2015 (Inventor—Blotsky et al.) (6 pages).
Response to Non-Final Office Action dated Sep. 17, 2015 for U.S. Appl. No. 14/717,660, filed May 20, 2015 and published as US 2015/0250817 on Sep. 10, 2015 (Inventor—Blotsky et al.) (9 pages).
Notice of Allowance dated Sep. 30, 2015 for U.S. Appl. No. 14/717,660, filed May 20, 2015 and published as US 2015/0250817 on Sep. 10, 2015 (Inventor—Blotsky et al.) (8 pages).
Restriction Requirement dated Dec. 15, 2009 for U.S. Appl. No. 12/249,798, filed Oct. 10, 2008 (Inventor—Blotsky et al.) (8 pages).
Response to Restriction Requirement dated Feb. 11, 2010 for U.S. Appl. No. 12/249,798, filed Oct. 10, 2008 (Inventor—Blotsky et al.) (7 pages).
Non-Final Office Action dated Apr. 9, 2010 for U.S. Appl. No. 12/249,798, filed Oct. 10, 2008 (Inventor—Blotsky et al.) (16 pages).
Response after Non-Final Action dated Jul. 9, 2010 for U.S. Appl. No. 12/249,798, filed Oct. 10, 2008 (Inventor—Blotsky et al.) (11 pages).
Final Office Action dated Jul. 14, 2010 for U.S. Appl. No. 12/249,798, filed Oct. 10, 2008 (Inventor—Blotsky et al.) (13 pages).
Response to Final Office Action dated Oct. 14, 2010 for U.S. Appl. No. 12/249,798, filed Oct. 10, 2008 (Inventor—Blotsky et al.) (8 pages).
Non-Final Office Action dated May 12, 2014 for U.S. Appl. No. 12/249,798, filed Oct. 10, 2008 (Inventor—Blotsky et al.) (8 pages).
Response to Non-Final Office Action dated Aug. 8, 2014 for U.S. Appl. No. 12/249,798, filed Oct. 10, 2008 (Inventor—Blotsky et al.) (7 pages).
Notice of Allowance dated Aug. 25, 2014 for U.S. Appl. No. 12/249,798, filed Oct. 10, 2008 (Inventor—Blotsky et al.) (8 pages).
Issue Notification dated Dec. 17, 2014 for U.S. Appl. No. 12/249,798, filed Oct. 10, 2008 (Inventor—Blotsky et al.) (1 page).
Preliminary Amendment dated Feb. 20, 2015 for U.S. Appl. No. 14/553,420, filed Nov. 25, 2014 now U.S. Pat. No. 9,107,869 on Aug. 18, 2015 (Inventor—Blotsky et al.) (6 pages).
Notice of Allowance and Examiner Initiated Interview Summary dated Apr. 13, 2015 for U.S. Appl. No. 14/553,420, filed Nov. 25, 2014 now U.S. Pat. No. 9,107,869 on Aug. 18, 2015 (Inventor—Blotsky et al.) (6 pages).
Issue Notification dated Aug. 18, 2015 for U.S. Appl. No. 14/553,420, filed Nov. 25, 2014 now U.S. Pat. No. 9,107,869 on Aug. 18, 2015 (Inventor—Blotsky et al.) (1 page).
Preliminary Amendment dated Oct. 22, 2015 for U.S. Appl. No. 14/806,461, filed Jul. 22, 2015 (Inventor—Blotsky et al.) (5 pages).
Requirement for Restriction/Election dated Jun. 2, 2011 for U.S. Appl. No. 12/497,387, filed Jul. 2, 2009 (Inventor—Blotsky et al.) (9 pages).
Response to Requirement for Restriction/Election dated Dec. 2, 2011 for U.S. Appl. No. 12/497,387, filed Jul. 2, 2009 (Inventor—Blotsky et al.) (11 pages).
Non-Final Office Action dated Dec. 27, 2011 for U.S. Appl. No. 12/497,387, filed Jul. 2, 2009 (Inventor—Blotsky et al.) (7 pages).
Response to Non-Final Office Action dated Mar. 26, 2012 for U.S. Appl. No. 12/497,387, filed Jul. 2, 2009 (Inventor—Blotsky et al.) (10 pages).
Non-Final Office Action dated Aug. 1, 2012 for U.S. Appl. No. 12/497,387, filed Jul. 2, 2009 (Inventor—Blotsky et al.) (8 pages).
Notice of Abandonment dated Feb. 19, 2013 for U.S. Appl. No. 12/497,387, filed Jul. 2, 2009 (Inventor—Blotsky et al.) (2 pages).
Non-Final Office Action dated Oct. 30, 2012 for U.S. Appl. No. 13/239,290, filed Sep. 21, 2011 now U.S. Pat. No. 9,180,141 on Nov. 10, 2015 (Inventor—Blotsky et al.) (13 pages).
Response to Non-Final Office Action dated Apr. 29, 2013 for U.S. Appl. No. 13/239,290, filed Sep. 21, 2011 now U.S. Pat. No. 9,180,141 on Nov. 10, 2015 (Inventor—Blotsky et al.) (16 pages).
Final Office Action dated Jul. 16, 2013 for U.S. Appl. No. 13/239,290, filed Sep. 21, 2011 now U.S. Pat. No. 9,180,141 on Nov. 10, 2015 (Inventor—Blotsky et al.) (15 pages).
Response to Final Office Action and Request for Continued Examination dated Nov. 22, 2013 for U.S. Appl. No. 13/239,290, filed Sep. 21, 2011 now U.S. Pat. No. 9,180,141 on Nov. 10, 2015 (Inventor—Blotsky et al.) (20 pages).
Non-Final Office Action dated Jul. 7, 2014 for U.S. Appl. No. 13/239,290, filed Sep. 21, 2011 now U.S. Pat. No. 9,180,141 on Nov. 10, 2015 (Inventor—Blotsky et al.) (22 pages).
Response to Non-Final Office Action dated Oct. 7, 2014 for U.S. Appl. No. 13/239,290, filed Sep. 21, 2011 now U.S. Pat. No. 9,180,141 on Nov. 10, 2015 (Inventor—Blotsky et al.) (22 pages).
Final Office Action dated Jan. 6, 2015 2014 for U.S. Appl. No. 13/239,290, filed Sep. 21, 2011 now U.S. Pat. No. 9,180,141 on Nov. 10, 2015 (Inventor—Blotsky et al.) (17 pages).
Response After Final Office Action and After Final Consideration Program Request dated Mar. 6, 2015 2014 for U.S. Appl. No. 13/239,290, filed Sep. 21, 2011 now U.S. Pat. No. 9,180,141 on Nov. 10, 2015 (Inventor—Blotsky et al.) (18 pages).
Advisory Action, Examiner Initiated Interview Summary, and After Final Consideration Program Decision dated Mar. 24, 2015 for U.S. Appl. No. 13/239,290, filed Sep. 21, 2011 now U.S. Pat. No. 9,180,141 on Nov. 10, 2015 (Inventor—Blotsky et al.) (3.
Response After Final Office Action dated Apr. 6, 2015 for U.S. Appl. No. 13/239,290, filed Sep. 21, 2011 now U.S. Pat. No. 9,180,141 on Nov. 10, 2015 (Inventor—Blotsky et al.) (18 pages).
Advisory Action dated May 1, 2015 for U.S. Appl. No. 13/239,290, filed Sep. 21, 2011 now U.S. Pat. No. 9,180,141 on Nov. 10, 2015 (Inventor—Blotsky et al.) (4 pages).
Response After Final Office Action and After Final Consideration Program Request dated Jun. 8, 2015 for U.S. Appl. No. 13/239,290, filed Sep. 21, 2011 now U.S. Pat. No. 9,180,141 on Nov. 10, 2015 (Inventor—Blotsky et al.) (18 pages).
Examiner Initiated Interview Summary and After Final Consideration Program Decision dated Jul. 15, 2015 for U.S. Appl. No. 13/239,290, filed Sep. 21, 2011 now U.S. Pat. No. 9,180,141 on Nov. 10, 2015 (Inventor—Blotsky et al.) (2 pages).
Notice of Allowance dated Jul. 15, 2015 for U.S. Appl. No. 13/239,290, filed Sep. 21, 2011 now U.S. Pat. No. 9,180,141 on Nov. 10, 2015 (Inventor—Blotsky et al.) (10 pages).
Notice of Allowance dated Aug. 11, 2015 for U.S. Appl. No. 13/239,290, filed Sep. 21, 2011 now U.S. Pat. No. 9,180,141 on Nov. 10, 2015 (Inventor—Blotsky et al.) (4 pages).
Issue Notification dated Nov. 10, 2015 for U.S. Appl. No. 13/239,290, filed Sep. 21, 2011 now U.S. Pat. No. 9,180,141 on Nov. 10, 2015 (Inventor—Blotsky et al.) (1 page).

\* cited by examiner

Figure 1A. Summary of Quantitative Data for Chickens on Water

Figure 1B

Summary of Quantitative Data for Chickens on Water

Figure 1C: Summary of Quantitative Data for Chickens on Extracted Mineral Element Composition (EiMEC) in Water

Figure 1D

Average Dressed Weights* for Chickens on Water or Extracted Mineral Element Composition (EMEC) in Water

| Group | Week No. | Avg. Dressed Weight (pounds) | % Greater Wt. with Extracted Mineral Element Composition (EMEC) in Water |
|---|---|---|---|
| Water | 5 | 1.7 (n = 14) | |
| EMEC in Water | 5 | 1.8 (n = 14) | +5.9 |
| Water | 6 | 2.6 (n = 9) | |
| EMEC in Water | 6 | 2.9 (n = 9) | +11.5 |
| Water | 7 | 2.8 (n = 12) | |
| EMEC in Water | 7 | 3.2 (n = 12) | +14.3 |

* Dressed Weights: Chickens were weighed after removal of skin, necks, and feet. Dressed weight chickens in the two groups did not different significantly before week no. 5

Figure 8

METHODS AND COMPOSITIONS FOR ANIMAL FEED

CROSS-REFERENCE TO RELATED APPLICATIONS

This application is a continuation of and claims priority to U.S. patent application Ser. No. 14/790,798, filed Jul. 2, 2015, which is a continuation of U.S. patent application Ser. No. 13/239,290 filed Sep. 21, 2011, now U.S. Pat. No. 9,180,141; which claims the priority of U.S. Provisional Application No. 61/385,064, filed Sep. 21, 2010, both of which are incorporated herein by reference in their entirety.

TECHNICAL FIELD

The present invention is directed to compositions and methods for improved meat and egg production, and improved animal feed supplements. Particularly, the invention comprises providing an extracted mineral element composition to animals, birds, fish, reptiles, livestock and pets.

BACKGROUND OF THE INVENTION

Animals are essential for human life. Besides the pleasurable aspects derived from living and working with animals and observing wildlife, animals are a major food source for humans and may also be used to provide wearable articles. For mass consumption, animals are generally raised in large scale production facilities, in contrast to farming practices in past times where animals were raised in smaller farming operations. Large scale production facilities with their attendant crowding of animals, increased infection control, and stressful lifestyle for the animals, require more human control of the animals' environment and diet.

An example of large scale production of animal husbandry is production of poultry. Poultry production comprises two major categories, meat production and egg production. Poultry production encompasses a number of different species, including chickens reared for laying eggs (i.e., "layers") and chickens reared for meat production (i.e., "broilers"), turkeys, ducks, and other waterfowl and game birds. The particular type of production may differ for each species though aspects are common to all.

Eggs are typically collected from breeder farms, taken to a hatchery and stored from 0 to 10 days prior to being set in an incubator. When the eggs are placed in incubators, embryonic development begins. Different species of birds require different incubation times. Chickens hatch in 21 days while turkeys and ducks need 28 days. Artificial incubation allows for the hatching of large numbers of chicks of the same age. Eggs are set in specially designed trays that allow the eggs to be tilted and turned. Eggs are transferred from setting trays into hatching trays 3 days before expected hatch. The hatchlings (chicks, poults, or ducklings) are processed (vaccinated, gender sorted, and/or other procedures) then transported to commercial grow-out facilities.

Chickens are specifically bred to have characteristics that are desirable in the final product. Meat poultry is selected for good meat type, fast growth, disease resistance, and efficient conversion of feed to meat. The body weights of meat and egg production strains are generally quite different. Meat production birds, i.e., broilers, are relatively easy to raise. When the birds arrive, they are placed into brooder rings around a heater (brooder) and introduced to waterers and feed. Generally, broilers are brooded in a portion of the house until a certain age before being given access to the entire barn.

Some farms separate male and female birds, a practice called separate-sex feeding. When birds are separated and fed according to gender (versus rearing males and females together), there will be more uniformity among males and among females in the flock. Separation of the birds also allows producers to feed diets that more closely meet the nutritional needs of the male and female birds.

Raising turkeys takes more time than raising broilers, as turkeys take longer to mature. Generally, a turkey is sent to market anywhere between 15 and 25 weeks of age. At 20 weeks of age, a male turkey should weigh about 35-40 pounds. The duck is a rapidly growing animal. A typical duck will weigh 7 pounds in only 6 or 7 weeks.

Different strains of chickens are used for table egg production. These are selected for high egg production, large egg size, and small body weight for better conversion of feed to eggs and good livability. The modern laying hen begins laying eggs at approximately 18 weeks of age and by the end of her first year, she may have produced upwards of 200 eggs—nearly 25 pounds. The hen reaches peak egg production (e.g., >95% or 95+%) within 4 to 6 weeks after she begins to lay eggs.

Poultry diets generally consist of common grains and protein sources with mineral and vitamin supplements. Animal or vegetable fats may be added to increase energy and reduce dustiness. Corn, grain sorghum, wheat, oats, and barley are often used for poultry feeding in the United States. Soybean meal is widely used as a protein supplement. Other important protein supplements are meat meal, fish meal, safflower meal, feather meal, and canola meal.

What is needed are food and/or water supplements or additives that can increase the meat production or egg laying capacity, enhance the overall health of the animals and lower the costs of raising poultry. Such methods and compositions would be advantageous for other livestock or animals.

SUMMARY

The present invention comprises methods and compositions for production of meat, milk and eggs. The methods and compositions are beneficial for all animals, whether companion animals, working animals or livestock animals. Examples are provided herein for poultry production, though the invention contemplates use in other animals.

The present invention comprises methods and compositions for increased survival rate of young animals. For example, methods and compositions comprise providing an extracted mineral element composition as taught herein to baby chicks to increase survival rate of the baby chicks.

The present invention comprises methods and compositions for increased growth rate of animals. For example, methods and compositions comprise providing an extracted mineral element composition as taught herein to chickens to increase growth rates. Chickens treated by such methods with such compositions reach harvest weight more quickly. For example, after five weeks of providing an extracted mineral element composition with feed and/or water, or separately alongside feed or water, the chickens, on average, weighed five pounds, which is an increase in weight compared to chickens not fed an extracted mineral element composition.

The present invention comprises methods and compositions for increasing the useful production time period and the lifespan of an animal. For example, methods and compositions comprise providing an extracted mineral element composition as taught herein to laying hens to increase the number of months and/or years that the hens lay eggs. Typically, laying hens are removed from production every year. For example, after feeding laying hens an extracted mineral element composition of the present invention, hens that were three years old were continuing to lay eggs.

The present invention comprises methods and compositions for improved egg production. For example, methods and compositions comprise providing an extracted mineral element composition as taught herein to laying hens for eggs with a firmer shell. Eggs with a firmer shell are less apt to break in shipping, thus resulting in a higher yield of eggs better able to survive handling during shipping and receipt.

The present invention comprises methods and compositions for increasing the hatch rate of poultry. For example, methods and compositions comprise providing an extracted mineral element composition as taught herein to breeder chickens for increased hatch rates. Additionally, chicks born from such breeder chickens are stronger and a larger number of the hatch group survive.

The present invention comprises methods and compositions for improving feed conversion. For example, methods and compositions comprise providing an extracted mineral element composition as taught herein to poultry for increased feed conversion.

The present invention comprises methods and compositions for reducing or preventing infection. For example, methods and compositions comprise providing an extracted mineral element composition as taught herein to poultry for reducing or preventing infection in poultry.

Methods and compositions of the present invention comprise providing an extracted mineral element composition in feed and/or water provided to the animals, or in a composition separate from feed or water. An extracted mineral element composition may be provided with continuously available feed or water, or may be provided at specific time points or for long or short durations.

DESCRIPTION OF THE FIGURES

FIGS. 1A and 1B show quantitative data for vaccinated and non-vaccinated chickens across several weeks for chickens on water. FIGS. 1C and 1D show quantitative data for vaccinated and non-vaccinated chickens across several weeks for chickens on extracted mineral element composition in water.

FIG. 8 shows the average dressed weights over several weeks for chickens on water and for chickens on extracted mineral element composition in water.

DETAILED DESCRIPTION

Figure 2:
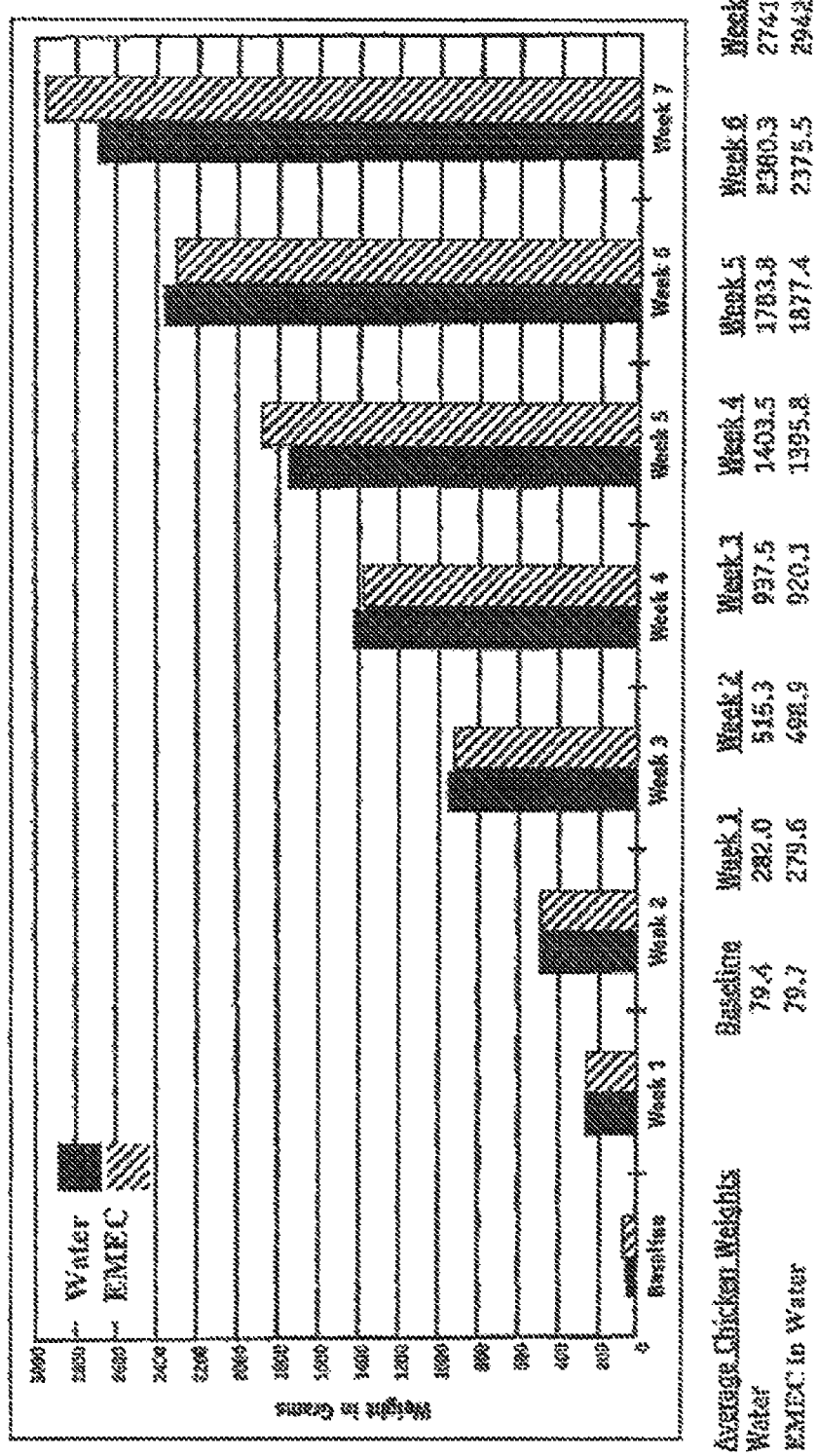
FIG. 2 shows the average body weight over several weeks for chickens on water and for chickens on extracted mineral element composition in water.

The present invention comprises methods and compositions for production of meat, milk and eggs. The present invention comprises methods and compositions for nutritional enrichment of foodstuffs such as, but not limited to, pork, beef, poultry and the like and comprises use of feed or water supplements formulated for feeding to animals at predetermined stages of growth or at all stages of growth. Whilst the supplement and formulae of the present invention are suitable as feed for producing beef, milk, pigs, goats, sheep, lamb, fish, poultry, including meat and eggs, and enhancing the health of household pets, rodents, monkeys, zoo animals, reptiles, and other living organisms under human control, the invention will mainly be described with reference to its application in raising poultry. The term poultry is generally used for all sort of breeds of domesticated birds independent of their age, comprising chickens, ducks, geese, fowl, pigeons, turkeys, and ostriches.

Methods and compositions of the present invention comprise providing feed or water comprising an extracted mineral element composition to livestock. Methods and compositions of the present invention comprise providing a composition comprising an extracted mineral element composition in addition to and separate from water or feed provided to livestock. Compositions comprising an extracted mineral element composition are formulated for systemic administration, such as oral administration, to poultry, e.g., via feed or water. The feed or water compositions, or a composition comprising an extracted mineral element composition separate from the feed or water, can be formulated along with customary excipients that are physiologically well-tolerated by birds in suitable forms such as capsules, powders, liquids, emulsions such as oil-in-water and water-in-oil, and suspensions, or an extracted mineral element composition may be provided in the form of a poultry feed supplement, poultry feed or provided in water compositions, or in liquid form in addition to water. The quantity of the mineral compositions are provided in terms of ppm in feed or water and can vary depending on the age of the animal, use and bird species. The present invention contemplates feed in forms known to those skilled in livestock, e.g., poultry, production and includes, but is not limited to, forms of feed, such as in pellets, chips and the like.

An aspect of the present invention comprises feed supplements for poultry in commercial poultry facilities. An example of use of compositions comprising an extracted mineral element composition in breeder chickens is herein provided, but is in no way a limitation of the invention. Compositions comprising an extracted mineral element composition may be used in methods including, but not limited to providing breeder chickens, egg laying chickens and meat production chickens, and all other types of poultry and other animals.

A primary objective of a poultry breeder operation is to produce fertile eggs that will be hatched to produce chicks for broiler operations and future breeder operations. Any reduction in rate of egg production and/or egg fertility, due to physiological or environmental impacts, can reduce operation efficiency and increase costs. Typically, egg fertility is equated to the percentage of eggs that hatch into viable chicks. Methods of the present invention comprise increasing hatch rate or egg fertility by providing to breeder chickens, in feed or water compositions, or in separate supplementation compositions, compositions comprising an extracted mineral element composition. Increase of hatch rate is determined by measuring the hatch rate for birds that do not receive an extracted mineral element composition compared to those birds that receive an extracted mineral element composition.

Animal husbandry of poultry breeder birds is typically carried out in two stages. The first is a development stage during which the chicks are grown into "pullets". Breeder bird chicks are grown for a period of 22 to 24 weeks in communal pens. Birds are fed a diet formulated to promote longevity and control weight gain of both males and females. Methods of the present invention comprise increasing the survival rate of chicks by providing to the chicks a feed or drink composition, or a separate composition, such compositions comprising an extracted mineral element composition. At the conclusion of this stage of development, the pullets are ready for the next stage.

The pullets are transferred to breeder houses for the remainder of their lives. Birds are typically maintained in the breeder house for 30 to 35 weeks. Females and males are placed separately into the houses. Methods of the present invention comprise feeding pullets by providing to the pullets a feed or drink composition, or a separate composition, such compositions comprising an extracted mineral element composition. A goal of breeder operations is to achieve good mating and egg laying behaviors of mature birds. Methods of the present invention comprise increasing mating and egg laying behaviors of mature birds by providing to the birds a feed or drink composition, or a separate composition, such compositions comprising an extracted mineral element composition. Newly placed female pullets come into egg laying maturity after 5 to 6 weeks in the breeder house environment. In traditional breeder operations, when females come into egg laying maturity, the females frequent nesting boxes. Each female can lay 1 to 3 eggs per day. Egg production per bird peaks at 10 to 12 weeks after placement and slowly declines thereafter. Eggs are laid in the nest boxes or on the floor and must be collected daily. Reduction in mating behavior ultimately reduces egg fertility. The breeder house manager monitors egg fertility often, typically weekly. Reduced egg fertility results in removal of non-mating males with replacement by fresh male pullets, called spiking, in order to restore normal mating behavior throughout the house. Methods of the present invention comprise decreasing the need for spiking by providing the birds a feed or drink composition, or a separate composition, such compositions comprising an extracted mineral element composition. Methods of the present invention comprise prolonging the egg fertility of birds by providing to the birds a feed or drink composition, or a separate composition, such compositions comprising an extracted mineral element composition.

The present invention provides methods and compositions that positively impact bird health with the use of an extracted mineral element composition. This includes a diet supplement or additive for poultry for poultry feed or water comprising an extracted mineral element composition. Incorporation of an extracted mineral element composition into bird rations improves bird health due to improvements in cardiovascular health and feed conversion. For example, the red color of male bird's combs and wattles is a general indicator of good bird health. Birds in physiological decline often show a purple comb/wattle color. Bird house managers often change diet formulations and daily rations in response to observation of purple comb/wattle color. Incorporation of an extracted mineral element composition into bird diets applies to both male and female birds and is useful for reducing mortality of aged birds. Specifically, an extracted mineral element composition supplemented diet improves male bird health for improving mating behavior over a longer period of time, and reduces the need to "spike" males during a breeder cycle.

In general, feed or water comprising an extracted mineral element composition impacts breeder bird performance in multiple ways. These include improvement of cardiovascular health and feed conversion; reduced rate of infection; reduced mortality of males and females; improved longevity of male mating behavior; reduced need to spike males; and improved egg laying productivity of females. Feed or water additive or supplement compositions of the present invention are advantageous to bird health in positively impacting mortality or related bird health issues. Poultry can experience cardiovascular difficulties, leading to bird death or poor mating performance or egg production and weight.

Feed or water compositions comprising an extracted mineral element composition, or a separate supplement composition comprising an extracted mineral element composition according to the present invention can provide advantageous feed conversion results while maintaining bird weight characteristics. Bird weight is determined by body weight measurement, typically done by measuring the weight of each bird. Feed performance data for feed or water comprising an extracted mineral element composition, or a separate composition comprising an extracted mineral element composition, according to the present invention exhibit improved feed conversion values and improved adjusted feed conversion values, wherein the average adjusted feed conversion value is defined as a ratio of a total feed consumption for the poultry over a time period to a total weight gain of the poultry over the time period after removal of a weight of any poultry that died during the time period.

The present invention comprises compositions and methods for increasing the live weight of poultry. Methods and compositions of the present invention comprise providing compositions comprising an extracted mineral element composition and methods for treating animals with compositions comprising an extracted mineral element composition to increase growth and weight gain. Compositions and methods for increasing the live weight of poultry are convenient and economical to administer. Compositions and methods for increasing the live weight of poultry are easy and economical to manufacture.

For example, the present invention comprises a livestock feed or water composition comprising an extracted mineral element composition for inclusion in the diet of livestock, at any time prior to slaughter, for the production of meat or eggs for human consumption, the feed or water composition comprising an extracted mineral element composition as disclosed herein. Feeding comprises any time up to and including immediately prior to slaughter of the livestock for meat produce. A livestock feed or water composition may comprise from 0.001% to 100% of the total dietary intake of the animal.

The present invention comprises a method of feeding livestock or poultry prior to slaughter of the livestock or poultry for production of meat for human consumption, the method comprising, a) preparing or providing an animal feed or water composition comprising an effective amount of an extracted mineral element composition for inclusion in the diet of livestock or poultry, and b) feeding the livestock or poultry with the feed or water composition comprising an extracted mineral element composition up to and immediately prior to slaughter, such as at or for a particular time period or continuously.

The present invention comprises a method of feeding livestock or poultry prior to slaughter of the livestock or poultry for production of non-fertilized eggs for human consumption or for fertilized eggs for breeder purposes, the method comprising, a) preparing or providing an animal feed or water composition comprising an extracted mineral element composition for inclusion in the diet of livestock or poultry, and b) feeding the livestock with the feed or water composition comprising an effective amount of an extracted mineral element composition up to and immediately prior to slaughter, such as at or for a particular time period or continuously.

A particular time period may comprise a growth period for the animals, a span of time of confinement for the animals, or may be a regular or irregular time period in which the composition is provided. Continuously may comprise every day for every feeding or watering period, or may comprise all or some of a particular feeding or watering schedule, such as every evening or every morning, or alternating patterns of evening or morning. The methods may comprise providing a composition that is separate from the feed or water that comprises an extracted mineral element composition. Such a separate composition comprising an extracted mineral element composition may be provided at the same time that feed or water is provided or at times different from when feed or water is provided.

The present invention comprises a method of feeding livestock or poultry using an extracted mineral element composition, for inclusion in the diet of livestock or poultry for the production of meat for human consumption, the method comprising providing an extracted mineral element composition in feed or water compositions, or in a composition separate from feed or water, to livestock, and allowing the livestock to eat or drink the extracted mineral element composition. The feed or water comprising an extracted mineral element composition may comprise 0.001% to 100% of the dietary intake of the livestock or poultry. The present invention comprises a method of feeding livestock or poultry comprising providing or administering an effective amount of an extracted mineral element composition for inclusion in the diet of livestock or poultry for the production of fertilized eggs for breeder production or unfertilized eggs for human consumption, the method comprising providing an effective amount of an extracted mineral element composition in feed or water compositions, or in a composition separate from feed or water, to livestock or poultry, and allowing the livestock or poultry to eat or drink the extracted mineral element composition.

The present invention comprises methods for making feed compositions comprising an extracted mineral element composition. An extracted mineral element composition may be added to standard feed compositions as are generally used for a particular animal, including age and sex specific feeds, resulting in a supplemented feed. An extracted mineral element composition may be added during the mixing of ingredients of the feed at a feed mill, and the extracted mineral element composition may be provided in a dry, liquid or steam form. An extracted mineral element composition may be added to pre-formed feed pellets or chips in a dry or liquid form as a finishing step prior to packaging the feed, or at any other desired step in making the feed. An extracted mineral element composition may be added to the feed by the poultry producer at one or more of the large scale production facilities before providing the supplemented feed. An extracted mineral element composition may be sprayed onto a processed animal feed product, including chips or pellets, at any point in the production cycle for feed material. An extracted mineral element composition may be sprayed onto feed once it is provided to the animals, and may be provided continuously or intermittently. An extracted mineral element composition may be provided along side the feed, and not incorporated or added directly to the feed, and may be provided in dry or liquid form, or may be admixed or incorporated with other supplementation compositions provided to the animals.

A supplemented water composition may be made by admixing a dry or a liquid form of an extracted mineral element composition with water and providing the supplemented water composition to animals in all available water. Supplemented water comprising an extracted mineral element composition may be provided continuously or on a schedule or intermittently as desired by the livestock producer.

The present invention comprises feed or water compositions, or separate compositions comprising an extracted mineral element composition wherein the concentration of the extracted mineral element composition is from about 0.0001% w/w to about 100% w/w of the composition. Ranges contained therein are contemplated by the present invention and include, but are not limited to, from about 0.0001% w/w to about 50% w/w of the composition; from about 0.001% w/w to about 10% w/w of the composition; from about 0.1% w/w to about 100% w/w of the composition; from about 0.1% w/w to about 10% w/w of the composition; from about 1% w/w to about 100% w/w of the composition; from about 1% w/w to about 20% w/w of the composition; from about 20% w/w to about 50% w/w of the composition; from about 50% w/w to about 100% w/w of the composition; and all amounts therein between. An extracted mineral element composition concentration in a feed or water composition may be 0.001%, 0.01%, 0.1%, 1%, 2.5%, 5%, 10%, 15%, 20%, 25%, 30%, 35%, 40%, 45%, 50%, 55%, 60%, 70%, 80%, 90% or 100% w/w of the composition.

A method of making a feed composition comprising an extracted mineral element composition comprises some or all of the following steps. A poultry feed generally consists of pellets that are usually produced by feed mills. Ground cereal may be used as base. To that base other constituents such as oil and vegetable and animal proteins are added. To this mix, a dry powdered form of an extracted mineral element composition or a liquid form of an extracted mineral element composition is added. The dry or liquid extracted mineral element composition may be added in an amount of about 0.001% w/w to about 50% w/w to the mixture. All the constituents are intimately mixed together in a grinding or mixing apparatus, sprayed with water or treated with steam and, at elevated temperature, extruded, i.e., pressed, through a nozzle having a diameter of from about 2 to about 15 mm.

During that pressing process, the moistened material is compacted and it leaves the nozzle in the form of a relatively hard bar, which at the nozzle outlet is cut using a cutting apparatus into pieces of desired length, for example from about 5 to about 25 mm in length. The resulting pellets, which are still warm, dry in the air as they are transported away or are taken on a conveyor belt through a heating chamber and dried at about from 80 to 120° C. The finished pellets are rod-shaped or cylindrical; they have a relatively smooth surface and are readily pourable without crumbling or forming dust. They generally have a density of about 1.2 g/cm$^3$.

An extracted mineral element composition may be added to the feed composition in the water or steam described above. Those skilled in the art can determine the amount of a dry or liquid extracted mineral element composition to add to the feed to result in a desired final concentration of extracted minerals.

The pellets are allowed to cool to room temperature and are packed in paper sacks or other suitable containers for storage or for transportation to the end consumer. No special precautionary measures are necessary because the pellets are generally storage-stable.

An extracted mineral element composition can be simply admixed with normal dry or wet poultry food or drinking water in amounts to yield the desired concentration of extracted minerals.

An extracted mineral element composition of the present invention and methods for making and using such an extracted mineral element composition are taught in U.S. patent application Ser. Nos. 10/752,729; 11/472,536; 11/638,311; 12/499,745; 12/497,387; and 12/249,798, and in continuation and divisional applications thereof, each of which is herein incorporated by reference in its entirety.

In general, an extracted mineral element composition is made by the following methods. The extraction techniques described herein relates in part to specific soils and soil combination compositions having taxonomic classifications including clay soil, sandy soil, and/or clay-sand soil comprising a combination of clay soil and sandy soil. Sandy soil typically is described as silicates. Soils classified as clay soils contain a significant percentage of clay in their composition, typically at least twenty percent by weight. A starting soil composition may comprise leonardite, or leonardite in combination with other soil types.

Soil includes very coarse, coarse, fine, very fine, and medium size particle sizes. The coarse particles range in size from 0.5-1.0 mm. The fine particles are from about 0.10-0.25 mm in size. The medium particles are from 0.25-0.50 mm in size. Very coarse particles are greater than about 1.0 mm in size. The very fine particles are less than about 0.10 mm in size.

The percent sand in clay-sand soil typically by definition equals or is greater than 20% by weight. The percent of silt in clay-sand soil typically by definition equals or is greater than 20% by weight.

Two samples of selected soil were analyzed by A&L laboratories in Memphis, Tenn. with the following results:

| Soil Sample Classification | | | |
|---|---|---|---|
| Site | % Clay | % Sand | % Silt |
| # 4 | 22.5 | 36.5 | 40.9 |
| # 5 | 23.1 | 24.4 | 52.5 |

The soils from Sites 4 and/or 5 or other sites were collected and subjected to the aqueous extraction process described below to produce both a liquid extracted mineral element composition containing mineral elements and to produce a dry powder extracted mineral element composition. The dry powder extracted mineral element composition is produced by drying the liquid mineral element composition.

Both the liquid extracted mineral element composition and the dry powder extracted mineral element composition capture and recover similar mineral elements to constitute an extracted mineral element composition. In an aspect, both liquid and dry powder extracted mineral element compositions produced by the procedures described in the referenced patent applications preferably, but not necessarily, comprise a minimum of 8 macro mineral elements and a minimum of 60 micro mineral elements. In an aspect, both liquid and dry powder extracted mineral element compositions produced by the procedures described in the referenced patent applications preferably, but not necessarily, consist of a minimum 8 macro mineral elements and a minimum of 60 micro mineral elements. In an aspect, both liquid and dry powder extracted mineral element compositions produced by the procedures described in the referenced patent applications preferably, but not necessarily, consist essentially of minimum of 8 macro mineral elements and at least a minimum 60 micro mineral elements.

Physical testing and analysis was also conducted on the liquid and dry extracted mineral element compositions. Typical specifications of liquid extract solution range in color but preferably are from yellow to amber brown and contain between 1-10% by weight of mineral elements, most preferably 3-5%. The solution is acidic with a pH ranging from 2.5-4.5, most preferably from 2.5-3.5. The liquid extract can be dried to produce an anhydrous powder. The anhydrous powder presently ranges in color from light-off-white to brown, but preferably from yellow to golden amber, is insoluble in any non-polar solvent such as hydrophobic liquids (oil and fats), is insoluble in alcohol, and is readily soluble, yet non-swelling, in water and hydro-alcoholic solutions at concentrations of 1-5%, most preferably at concentrations of 3-5% by weight. The dry powder extracted mineral element composition is partially soluble or capable of being partially suspended in polar solvent in supersaturated solutions. The dry powder can also be easily suspended in non-polar solvents.

Both liquid and dry extracted mineral element compositions produced by the procedures described in the referenced patent applications may comprise a minimum of 8 macro mineral elements and a minimum of 60 micro mineral elements, wherein the micro mineral elements include trace and rare earth mineral elements. Both liquid and dry extracted mineral element compositions produced by the procedures described in the referenced patent applications may consist of a minimum of 8 macro mineral elements and a minimum of 60 micro mineral elements, wherein the micro mineral elements include trace and rare earth mineral elements. Both liquid and dry extracted mineral element compositions produced by the procedures described in the referenced patent applications may consist essentially of a minimum of 8 macro mineral elements and a minimum of 60 micro mineral elements, wherein the micro mineral elements include trace and rare earth mineral elements.

For example, in an aspect, the dry extracted mineral element composition may comprise the macro mineral elements of calcium, chlorine, magnesium, manganese, phosphorous, potassium, silicon, and sodium, at concentrations ranging from 0.0001-20.00% by weight, most preferably from 0.001%-10% by weight, and, may comprise at least sixty micro mineral elements at concentrations ranging from 0.00001-3.0% by weight, most preferably from 0.0001-1% by weight. The micro mineral elements include aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, samarium, scandium, selenium, silver, strontium, sulfur, tantalum, terbium, tellurium, thallium, thorium, thulium, tin, titanium, tungsten, vanadium, ytterbium, yttrium, zinc, and zirconium.

In an aspect, the dry extracted mineral element composition may consist of the macro mineral elements of calcium, chlorine, magnesium, manganese, phosphorous, potassium, silicon, and sodium, at concentrations ranging from 0.0001-20.00% by weight, most preferably from 0.001%-10% by weight, and, may consist of at least sixty micro mineral elements at concentrations ranging from 0.00001-3.0% by weight, most preferably from 0.0001-1% by weight. The micro mineral elements include aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, samarium, scandium, selenium, silver, strontium, sulfur, tantalum, terbium, tellurium, thallium, thorium, thulium, tin, titanium, tungsten, vanadium, ytterbium, yttrium, zinc, and zirconium.

In an aspect, the dry extracted mineral element composition may consist essentially of the macro mineral elements of calcium, chlorine, magnesium, manganese, phosphorous, potassium, silicon, and sodium, at concentrations ranging from 0.0001-20.00% by weight, most preferably from 0.001%-10% by weight, and, may consist essentially of at least sixty micro mineral elements at concentrations ranging from 0.00001-3.0% by weight, most preferably from 0.0001-1% by weight. The micro mineral elements include aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, samarium, scandium, selenium, silver, strontium, sulfur, tantalum, terbium, tellurium, thallium, thorium, thulium, tin, titanium, tungsten, vanadium, ytterbium, yttrium, zinc, and zirconium.

Since the process described herein normally does not introduce any minerals as part of the extraction process, it can be established that any minerals identified and quantified by the process described herein have been captured and recovered from the initial soil matter or the starting raw material. Therefore, it can be established that the original clay or other soil that processed through the extraction method described herein likely include aluminum silicates and other metal silicates in nature which has been naturally enriched with multiple detectable minerals. It can also be established that if a mineral element is identified and quantified in the aqueous liquid extract, it will be identified and quantified in the dry powdered extract in much higher concentrations as a result of drying process or volume reduction.

For example, a lot produced using the soil and extractions methods described herein was tested by independent analytical testing for conducting chemical analysis using standard techniques of identification and quantification for both dry and liquid forms of the comprehensive mineral composition. The results of testing performed at Teledyne Wah Chang Laboratories in Huntsville, Ala., utilizing scientifically accepted and standard equipment such as Titration, Inductively Coupled Plasma, Mass Spectrometry, and Atomic Absorption equipment resulted in the mineral element quantification data set forth below in TABLE I for an aqueous mineral element composition and from the dry mineral element composition that resulted when the aqueous mineral element composition was dried to produce a powder.

TABLE I

Concentration of Elements in Aqueous Liquid Composition and in Dry Powder

| Element | Conc. in aqueous liquid composition | Conc. in dry powder |
|---|---|---|
| MACRO MINERAL ELEMENTS | | |
| Calcium | 2900 ppm | 8% |
| Chlorine | 170 mg/ml | 0.84%* |
| Magnesium | 460 ppm | 0.95% |
| Manganese | 8.6 ppm | 240 ppm |
| Phosphorous | 0.2 g/L | 0.43% |
| Potassium | 220 mg/L | 1.2% |
| Silicon | 130 mg/L | 0.36% |
| Sodium | 720 mg/L | 2.0% |
| MICRO MINERAL ELEMENTS | | |
| Aluminum | 540 ppm | 0.65% |
| Antimony | 460 ppb | 16.0 ppm |
| Arsenic | 11 ppm | 3.1 ppm |
| Barium | 340 ppb | 11.0 ppm |
| Beryllium | 0.29 ppm | .01 ppm |
| Bismuth | <50 ppb | <1.00 ppm |
| Boron | 2.0 mg/L | 72.00 ppm |
| Bromine | *Present as part of Chlorine assay | |
| Cadmium | <50 ppb | 1.10 ppm |
| Total Organic Carbon | 12 g/L | Trace |
| Cerium | 1600 ppb | 68.00 ppm |
| Cesium | 82 ppb | 2.00 ppm |
| Chromium | 1.8 ppm | 5.00 ppm |
| Cobalt | 0.25 ppm | 1.00 ppm |
| Copper | 0.09 ppm | <1.00 ppm |
| Dysprosium | 230 ppb | 9.00 ppm |
| Erbium | 150 ppb | 6.00 ppm |
| Europium | <50 ppb | 2.00 ppm |
| Fluorine | *Present as part of Chlorine assay | |
| Gadolinium | 220 ppb | 9.00 ppm |
| Gallium | 70 ppb | 2.40 ppm |
| Germanium | <50 ppb | <1.00 ppm |
| Gold | <50 ppb | <1.00 ppm |
| Hafnium | <0.5 mg/L | 5.00 ppm |
| Holmium | <50 ppb | 2.00 ppm |
| Iodine | *Present as part of Chlorine assay | |
| Indium | <50 ppb | Trace |
| Iridium | <50 ppb | <1.00 ppm |
| Iron | 730 ppm | 1.25% |
| Lanthanum | 650 ppb | 28.00 ppm |
| Lead | <50 ppb | <1.00 ppm |
| Lithium | 0.9 mg/L | <1.00 ppm |
| Lutetium | <50 ppb | <1.00 ppm |
| Mercury | Trace | <1.00 ppm |

TABLE I-continued

Concentration of Elements in Aqueous Liquid Composition and in Dry Powder

| Element | Conc. in aqueous liquid composition | Conc. in dry powder |
|---|---|---|
| Molybdenum | 3200 ppb | 120.00 ppm |
| Neodymium | 1000 ppb | 45.00 ppm |
| Nickel | 0.74 ppm | 2.00 ppm |
| Niobium | 96 ppb | 3.00 ppm |
| Palladium | <500 ppb | <1.00 ppm |
| Platinum | <50 ppb | <1.00 ppm |
| Praseodymium | 290 ppb | 10.00 ppm |
| Rhenium | <50 ppb | <1.00 ppm |
| Rhodium | <50 ppb | <1.00 ppm |
| Rubidium | 360 ppb | 11.00 ppm |
| Ruthenium | <50 ppb | <1.00 ppm |
| Samarium | 250 ppb | 10.00 ppm |
| Scandium | <400 ppb | 4.00 ppm |
| Selenium | 0.63 mg/L | 21.00 ppm |
| Silver | <0.02 ppm | <5.00 ppm |
| Strontium | 14000 ppb | 420.00 ppm |
| Sulfur | 1.1 g/L | 1.8% |
| Tantalum | <50 ppb | <1.00 ppm |
| Terbium | <50 ppb | 2.00 ppm |
| Tellurium | <50 ppb | <1.00 ppm |
| Thallium | <50 ppb | 1.00 ppm |
| Thorium | 640 ppb | 22.00 ppm |
| Thulium | <50 ppb | 1.00 ppm |
| Tin | <50 ppb | <1.00 ppm |
| Titanium | 9.34 ppm | 210.00 ppm |
| Tungsten | 52 ppb | 17.00 ppm |
| Vanadium | 4.3 ppm | 14.00 ppm |
| Ytterbium | 140 ppb | 6.00 ppm |
| Yttrium | 1300 ppb | 61.00 ppm |
| Zinc | 1.2 ppm | 14.00 ppm |
| Zirconium | 2.0 mg/L | 62.00 ppm |

The mineral element compositions set forth above in TABLE I were produced from naturally occurring soil the analysis of which is reflected below in TABLE II.

TABLE II

Analysis of Naturally Occurring Soil Macro Mineral Elements

| Element | Concentration in ppm by weight unless noted as % (for weight percent) |
|---|---|
| Silicon | 25.0% |
| Aluminum | 9.3% |
| Potassium | 4.8% |
| Magnesium | 0.83% |
| Sulfur | 1.6% |
| Iron | 1.6% |
| Calcium | 4.1% |
| Titanium | 0.23% |
| Sodium | 0.138% |
| Manganese | 150 |
| Gallium | 25 |
| Molybdenum | 61 |
| Germanium | 25 |
| Iodine | 7 |
| Bromine | 5.2 |
| Tungsten | 8.1 |
| Hafnium | 2.0 |
| Tantalum | 0.50 |
| Zirconium | 10 |
| Arsenic | 0.2 |
| Antimony | 29 |
| Selenium | 4.1 |
| Zinc | 20 |
| Samarium | 3.5 |
| Holmium | 1.1 |
| Terbium | 0.62 |
| Iridium | 0.51 |
| Lutetium | 0.45 |
| Chromium | 70 |
| Lanthanum | 18 |
| Ruthenium | 7.8 |
| Yttrium | 1.2 |
| Indium | 0.38 |
| Lead (under) | 17 |
| Niobium | 2.89 |
| Carbon | 0.19 |
| Hydrogen | 0.05 |
| Nitrogen | 0.03 |
| Scandium | 3.7 |
| Cobalt | 4.8 |
| Ytterbium | 1.4 |
| Strontium | 240 |
| Barium | 390 |
| Gold | .68 |
| Europium | .49 |
| Neodymium | 20 |
| Cerium | 40 |
| Cesium | 183 |
| Thorium | Above 100 |
| Uranium | Above 100 |
| Nickel | 60 |
| Beryllium | 0.10 |
| Bismuth | 14.3 |
| Boron | 7 |
| Cadmium | 1.12 |
| Chloride | 6100 |
| Copper | 2.2 |
| Fluoride | 3.85 |
| Lithium | 1.44 |
| Mercury | 0.166 |
| Palladium | 0.74 |
| Phosphate | 320 |
| Platinum | 0.08 |
| Rhodium | 0.44 |
| Rubidium | 36.5 |
| Silver | 0.3 |
| Tellurium | 0.1 |
| Thulium | 0.65 |
| Tin | 0.44 |
| Vanadium | 8 |
| Dysprosium | 4.0 |
| Praseodymium | 2.0 |
| Thallium | 10 |
| Rhenium | 1.0 |
| Erbium | 2.0 |
| Oxygen | 0.2 |

Once a desirable naturally occurring soil or soil combination is obtained, the soil(s) is subjected to the extraction process described in U.S. patent application Ser. No. 10/725,729 (see also FIG. 11 herein). The selection of an appropriate soil or soil combination is, however, important in the practice of the invention and this process is now described. It is understood that it is possible to incorporate synthetically produced "soils" or compositions to produce soils used in the invention; however, the use of naturally occurring soils is presently preferred and it is the use of such naturally occurring soils that is now described in detail.

Clay soils, mixtures of clay soils, or mixtures of clay soil(s) and leonardite are presently preferred in the practice of the invention. One reason such soil combinations are preferred is that such soils can be high in the mineral elements deemed important in the practice of the invention. As noted, it is preferred that mineral element compositions produced in accordance with the invention include at least eight macro mineral elements and at least sixty micro mineral elements.

The first step in determining whether a clay soil is acceptable is to determine of arsenic, lead, mercury, and cadmium are each present in acceptably small concentrations. It is presently preferred that the concentration of each of these elements be less than the concentrations shown below in TABLE III.

TABLE III

Maximum Desired Concentrations of Toxic Elements Maximum

| Element | Desired Soil Conc. (ppm or ppb) |
|---|---|
| Arsenic | 0.2 ppm |
| Lead | 0.17 ppb |
| Mercury | 0.116 ppm |
| Cadmium | 1.12 ppm |

To achieve the desired concentrations noted above, a soil that has a greater than desired concentration of the toxic elements can be admixed with one or more soils containing a lesser than desired concentration of the toxic elements. Further, the maximum desired concentrations of the four toxic elements noted above can vary depending on the intended end use of the mineral element composition produced by the invention. For example, if the mineral element composition is intended to be used in products ingested by human beings, the acceptable levels of the toxic elements normally will be less than if the mineral element composition will be used in agricultural products.

If the soil, or soil combination, has appropriately low concentrations of the four toxic elements arsenic, lead, mercury, and cadmium, the soil is next tested to determine if acceptable concentrations of rare earth elements are present in the soil or soil combination. Desired levels of rare earth elements are set forth below in TABLE IV.

TABLE IV

Preferred Minimum Concentrations of Selected Rare Earth Elements in Naturally Occurring Soil

| Element | Preferred Minimum Conc. (in ppm) |
|---|---|
| Cerium | 40 |
| Praseodymium | 2 |
| Neodymium | 20 |
| Samarium | 3.5 |
| Europium | 0.49 |
| Terbium | 0.62 |
| Dysprosium | 4 |
| Holmium | 1 |
| Erbium | 2 |
| Thulium | 0.65 |
| Ytterbium | 1.2 |

The concentration of the elements listed in TABLE IV can vary as desired, but, as noted, it is desirable to have at least the concentration of each element as noted in TABLE IV. A lanthanum concentration of at least eighteen (18) ppm and a scandium concentration of at least three and seven-tenths (3.7) ppm are also preferred. Concentrations of promethium and gadolinium are also desirable. In the practice of the invention, at least ten rare earth elements are present in the soil, preferably at least twelve, and more preferably all of the rare earth elements along with lanthanum and scandium. The presence of most or all of the rare earth elements in the soil, and in the mineral element compositions derived from the soil, is believed to be important in improving the efficacy of the mineral element composition when ingested by the body or when transdermally absorbed by the body.

The clay soil or soil combination also includes at least 5% by weight calcium, preferably at least 10% by weight calcium, and most preferably at least 20% by weight calcium. Concentrations of calcium of 25% by weight or greater are acceptable.

The clay soil or soil combination also includes at least 5% by weight silica, preferably at least 10% by weight silica, and most preferably at least 20% by weight silica. Concentrations of silica of 25% by weight or greater are acceptable.

The clay soil or soil combination also includes at least 0.25% by weight phosphorous, preferably at least 1% by weight phosphorous, and most preferably at least 2% by weight phosphorous.

Figure 11:
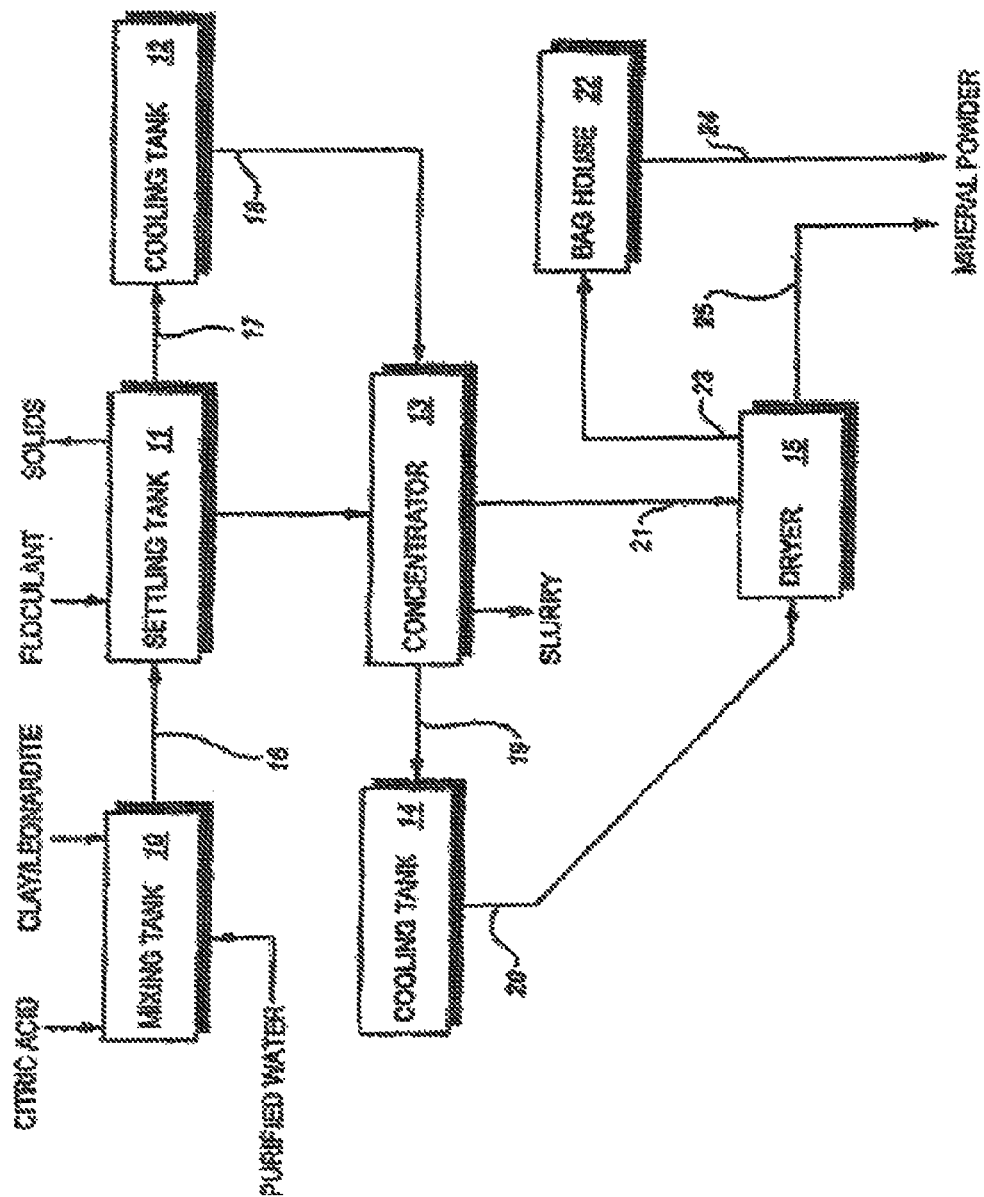
FIG. 11 shows a soil extraction process.

Leonardite is a valuable mineral source in producing soils that are subjected to the extraction process illustrated in FIG. 11.

Once a clay soil or clay soil combination is obtained that contains the requisite mineral elements, the clay soil is subjected to the extraction process of FIG. 1 of U.S. patent application Ser. No. 10/725,729, which is reproduced as FIG. 11 herein. The following example describes the extraction process by way of illustration, and not limitation of the invention.

In FIG. 11 of the present application, which represents an example of extraction process, 12,000 pounds of water purified via reverse osmosis or another desired purification process, 200 pounds of citric acid, and 5000 pounds of clay soil are added to the mixing tank 10. The amount of citric acid (or of phosphoric acid or other edible acid(s)) used can be in the range of 0.25% to 7.5% of the weight of water utilized, but typically is in the range of 1.0% to 2.0%. The purified water is produced using any desired water purification technique; however, water purified by reverse osmosis is presently utilized. The water-citric acid-soil slurry is gently agitated (for example, with a blade slowly rotating at from one to ten RPM) for about an hour, although the agitation time can vary as desired. The agitation is preferably non-cavitating and is carried out without forming bubbles in the mixture.

The slurry from tank 10 is directed, as indicated by arrow 16, into a settling tank 11 to permit particulate to settle downwardly out of the slurry. The slurry is maintained in the settling tank 11 for any desired length of time, but this length of time is presently in the range of about one to ten days. As the length of time that the slurry is maintained in the settling tank 11 increases, the amount of liquid that can be drawn out of the tank and sent to cooling tank 12 or concentrator 13 increases and the amount of solids that have settled to the bottom of the tank increases. Chemicals or any other desired method can be utilized to facilitate the settling of solids from slurry directed into tank 10. After the slurry has resided in settling tank 11 for the desired period of time, liquid is drawn out of the tank to cooling tank 12, or directly to the concentrator 13. The solids on the bottom of tank 11 can be directed to tank 10 to be reprocessed, can be discarded, or can be otherwise utilized.

Cooling tank 12 cools the fluid from tank 11 to a temperature in the range of forty to seventy degrees F. (5-21° C.). Tank 12 (and 14) is presently cooled with a refrigeration system to cool the fluid in tank 12. Consequently, when fluid contacts the inner cooled wall surfaces of tank 12, the wall surfaces transport heat away from and cool the fluid. Any desired system can be utilized to cool tank 12 (and 14) and/or to cool the fluid in the tank. For example, a coil can be placed in the fluid and cool the fluid without directly cooling the tank walls with refrigeration or other system. The fluid from tank 11 is cooled to prevent or minimize yeast and mold growth. The fluid in tank 11 normally is heated due to the ambient temperature and not due to any chemical or mechanical action that takes places in tank 11. Cooled liquid from tank 12 is, as indicated by arrow 18, directed from tank 12 to concentrator 13.

The concentrator 13 comprises a thin film composite reverse osmosis system in which fluid is directed into a plurality of long, cylindrical, hollow liquid permeable membrane tubes under pressure; and, in which fluid is forced radially out through the liquid permeable cylindrical membrane wall to increase the concentration of the mineral elements in the fluid. Evaporation is an alternate approach to increasing the concentration of mineral elements in the fluid. A reverse osmosis system is preferable to evaporation because it requires less energy, and because the water that passes radially through the membrane is a source of clean usable water.

One preferred reverse osmosis system includes eight hollow tubes or "vessels" that are about four inches in diameter and forty inches long. Each tube houses three concentric cylindrical membranes. The permeability flow rate is approximately 80% to 95% rejection, depending on the feed rate and the concentration of mineral elements in the fluid being treated. The spacing between the three concentric membranes is about ¼ inch. There are three ring couplers and one end plug per tube. The maximum pressure allowed by the cylindrical membranes is about 600 psig. A pressure of between 300 to 450 is recommended and is normally used. The membranes are to be utilized at a temperature of 135 degrees F. (57° C.) or less. The temperature of the fluid and the membrane is, however, typically maintained in the range of 55° F. to 65° F. (12-20° C.). The fluid from tank 11 is processed by passing it sequentially through each of the eight tubes.

If desired, concentration systems other than reverse osmosis systems can be utilized. Such other systems are not believed comparable to a reverse osmosis system in terms of cost and efficiency.

In FIG. 1 of U.S. patent application Ser. No. 10/725,729, which is reproduced herein as FIG. 11, the "slurry" by product produced by the concentrator 13 comprises clean usable water with a low concentration of mineral elements. The aqueous concentrate liquid produced by concentrator 13 is, as indicated by arrow 19, directed to cooling tank 14 or directly to dryer 15. Tank 14 cools the concentrate liquid to 40-70° F. (5-20° C.) to prevent the growth and yeast and mold.

The concentrate liquid produced by concentrator 13 has a pH of approximately 3. The concentrate liquid typically includes from three to twelve percent by weight mineral elements, i.e., if the mineral elements are separated from the concentrate liquid, a dry material is produced that has a weight equaling about 3% to 12% by weight of the concentrate liquid. The pH of the concentrate liquid is adjusted by varying the amount of citric acid or other edible acid and/or alkaline or acidic soil added to the mixing tank 10 and is in the range of pH 2.0 to pH 5.0, preferably pH 2.5 to pH 3.5. The pH of the concentrate liquid (and dry powder or other material produced therefrom) preferably is less than pH 4.5. TABLE I herein illustrates the mineral element present in one concentrate liquid produced by concentrator 13. If necessary, the concentrate liquid is recirculated back through concentrator 13 to increase the mineral element content in the liquid. As the proportion of mineral elements increases, the propensity of mineral elements to precipitate from the concentrate liquid increases. A mineral element concentration of at least eight percent is presently preferred for injection into dryer 15. A mineral element concentration in the range of three to twelve percent or more is beneficial because many prior art processes currently only produce a fluid having a mineral element concentration of about two percent.

Any desired drying system can be utilized. The present drying apparatus consists of a tower into which the concentrate fluid is sprayed. Air in the tower is heated. The concentrate fluid is sprayed in a pattern that causes the spray to swirl down the sides of the tower. As the spray travels down the sides of the tower, the water evaporates, producing powder particles including mineral elements. The powder falls downwardly to the bottom of the tower. Moist air travels upwardly through the center of the tower and is directed 23 to a bag house 22. The moist air enters elongate air-permeable hollow generally cylindrical bags in the bag house. The air travels outwardly through the walls of the bags and leaves behind powder particles on the inside surfaces of the bag. The bags are shaken each thirty seconds to cause the powder on the inner surfaces of the bag to fall downwardly for collection. TABLE I illustrates the mineral element concentration in the powder produced in dryer 15 when the liquid mineral element concentrate having the composition set forth in TABLE I was directed into dryer 15. The dry powder mineral element composition of TABLE I in aqueous solution has a pH of about 3.0.

In one spray system utilized in the dryer 15, the fluid concentrate is directed into dryer 15 under a pressure of about 2500 psi. The orifice size of the spray nozzles utilized is about 0.027 inch. The spray angle of the nozzle is 70 degrees and the average droplet size is about 75 microns.

Compositions of the present invention may comprise acceptable carriers. Compositions disclosed herein can be used in combination with an acceptable carrier. Suitable carriers and their formulations are described in Remington 1995, and refers to molecular entities and other ingredients of such compositions that are physiologically tolerable and do not typically produce untoward reactions (such as gastric upset, dizziness and the like) when administered.

As used herein, the term "carrier" applied to compositions of the invention refers to a diluent, excipient, or vehicle with which an extracted mineral composition is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable carriers are described in "Remington's Pharmaceutical Sciences" by E. W. Martin, 18th Edition.

Carriers are known to those skilled in the art. These most typically would be standard carriers for administration of compositions to humans or animals, including solutions such as sterile water, saline, and buffered solutions at physiological pH. Compositions may include carriers, thickeners, diluents, buffers, preservatives, surface active agents and the like in addition to the extracted mineral element composition. Compositions may further comprise one or more active ingredients such as antimicrobial agents, anti-inflammatory agents, anesthetics, and the like.

The composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The compositions can be administered intravenously, intraperitoneally, intramuscularly, subcutaneously, intracavity, or transdermally.

It will be understood that the embodiments of the present invention which have been described are illustrative of some of the applications of the principles of the present invention. Numerous modifications may be made by those skilled in the art without departing from the true spirit and scope of the invention. The term "effective" means that the amount of the composition used is of sufficient quantity to modulate, inhibit or increase, a characteristic or parameter of the subject or animal to which an effective amount of a composition was administered or provided. Such modulation only requires a reduction, increase or alteration, not necessarily elimination. Effective dosages and schedules for administering the disclosed compositions may be determined empirically, and making such determinations is within the skill in the art. The dosage ranges for the administration of the compositions are those large enough to produce the desired effect in the animal to which the composition was administered or provided. The dosage should not be so large as to cause adverse side effects. Generally, the dosage will vary with the age, condition, or sex of the animal, route of administration, or whether drugs are included in the regimen, and can be determined by one of skill in the art. Dosage can vary, and can be administered in one or more dose administrations daily, for one or several days. Guidance may be found in the literature.

An effective amount of a composition comprising the extracted mineral element composition for any particular animal will depend upon a variety of factors including the condition and result desired from the animal, the identity and activity of the specific composition employed; the age, body weight, general health, sex and diet of the subject or animal; the time of administration; the route of administration; the rate of excretion of the specific composition employed; the duration of the provision of the composition; drugs used in combination or coincidental with the specific composition employed and like factors well known in the veterinary arts.

For example, it is within the skill of the art to start doses of a composition comprising the extracted mineral element composition at levels lower than those required to achieve the desired effect and to gradually increase the dosage until the desired effect is achieved. One can also evaluate the particular aspects of the animal through techniques such as signs, symptoms, and objective laboratory tests that are known to be useful in evaluating the status of a animal. For example, if based on a comparison with an appropriate control group and/or knowledge of the normal progression of growth or production in the general population or the particular animal's physical condition is shown to be improved (e.g., weight is gained more rapidly), then a particular composition dosage and regimen will be considered efficacious. The same types of comparisons between groups or knowledge of normal growth or production may be used for determining efficacious treatments.

An effective amount of a disclosed composition comprising the extracted mineral element composition may be given daily, every other day, weekly, monthly, bi-monthly, every other monthly, yearly, or at any other interval that is determined by the caretaker or provider to be effective. For example, an effective daily dose can be divided into multiple doses for purposes of administration. Consequently, single dose compositions can contain such amounts or submultiples thereof to make up the daily dose. Disclosed compositions can also be administered as part of a combination of other administered compositions, such as feed and water. In an aspect, disclosed compositions can be administered to the subject prior to, subsequent to, concurrently with, or post treatment with other provided compositions. In an aspect, the animal receives both administrations on an alternating or rotating schedule. In an aspect, the animal receives a singular treatment with a disclosed composition. In an aspect, the animal receives at least one treatment with a disclosed composition. In an aspect, the animal receives at least one treatment with a disclosed composition and at least one other treatment.

In a further aspect, an effective amount can be determined by preparing a series of compositions comprising varying amounts of disclosed compositions such as an extracted mineral element composition and determining the functional or physical characteristics in vivo and in vitro and matching these characteristics with specific pharmaceutical delivery needs, for example, subject or animal body weight or physical condition.

Definitions

The terminology used herein is for the purpose of describing particular aspects only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, an aspect includes from the one particular value and/or to the other particular value. Similarly, when values are expressed as approximations, by use of the antecedent "about," it will be understood that the particular value forms an aspect. It will be further understood that the endpoints of each of the ranges are significant both in relation to the other endpoint, and independently of the other endpoint.

The word "or" as used herein means any one member of a particular list and also includes any combination of members of that list.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100%, or more, or any amount of promotion in between compared to native or control levels. In an aspect, the increase or promotion is 10-20, 20-30, 30-40, 40-50, 50-60, 60-70, 70-80, 80-90, or 90-100% as compared to native or control levels. In an aspect, the increase or promotion is 0-25, 25-50, 50-75, or 75-100%, or more, such as 200, 300, 500, or 1000% more as compared to native or control levels. In an aspect, the increase or promotion can be greater than 100 percent as compared to native or control levels, such as 100, 150, 200, 250, 300, 350, 400, 450, 500% or more as compared to the native or control levels.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Treating" or "treatment" of a state, disorder or condition includes: (1) preventing or delaying the appearance of clinical symptoms of the state, disorder or condition developing in an animal or bird such as poultry (e.g., chicken) that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

The benefit to animal or poultry (e.g., chicken) to be treated is either statistically significant or at least perceptible the caretaker, handler, farmer, veterinarian, etc.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the claims.

References, including patents, patent applications, and various publications are cited and discussed throughout the specification. The citation and/or discussion of such references is provided merely to clarify the description of the present invention and is not an admission that any such reference is "prior art" to the present invention. All references cited and discussed in this specification are each incorporated herein by reference in its entirety and to the same extent as if each reference was individually incorporated by reference.

EXAMPLES

Example 1—Egg and Chick Production

To determine the benefits of an extracted mineral element composition in primary layers in promoting egg production and hatching efficiency, primary breeders were maintained in appropriate housing conditions favorable for maximum laying. The primary breeders were supplemented with an extracted mineral element composition in liquid form via drink water lines at the rate of 1 ounce per gallon with continuous flow, cycled at 6 days on and 1 day off. To prevent the build up of foreign material or contaminating algae or bacteria, the one off day was used to clean and flush the water lines. Layers were retired at 75 weeks of age. The breeders were kept in two barns. In Barn 1 (LH-1), 10,000 birds had a laying percentage of approximately 83.8%. In Barn 2 (LH-2), 9,200 birds had a layer percentage of approximately 81.7%. The data for sixteen (16) different hatching dates is presented below.

TABLE V

Summary of Data for Layers

| Set Date | Barn #1 (LH-1) Hatch % | Barn #2 (LH-2) Hatch % |
| --- | --- | --- |
| Jan. 3, 2010 | 82.0 | 79.1 |
| Jan. 6, 2010 | 86.5 | 84.9 |
| Jan. 10, 2010 | 87.1 | 86.0 |
| Jan. 17, 2010 | 81.5 | 87.7 |
| Jan. 24, 2010 | 84.1 | 86.6 |
| Jan. 31, 2010 | 79.7 | 86.3 |
| Feb. 3, 2010 | 83.3 | 87.8 |
| Feb. 7, 2010 | 82.4 | 89.0 |
| Feb. 28, 2010 | 84.7 | 88.0 |
| Mar. 7, 2010 | 64.6 | 68.9 |
| Mar. 14, 2010 | 82.7 | 83.8 |
| Mar. 17, 2010 | 85.3 | 92.4 |
| Mar. 21, 2010 | 82.6 | 86.6 |
| Mar. 24, 2010 | 83.5 | 88.8 |
| Mar. 31, 2010 | 78.7 | 81.8 |
| Apr. 4, 2010 | 70.2 | 79.2 |

Based on these results, the laying efficiency for 80,000 birds was calculated. The laying efficiency per 80,000 birds laying at an average of 85% was equal to 68,000 eggs. The average hatching percentage was calculated from the difference between (LH-2)–(LH-1) starting at the first recorded hatching date (Jan. 17, 2010) through the last recorded hatching date (Apr. 4, 2010). The average hatching percentage for the control group was 80.3% and the average hatching percentage for the extracted mineral element composition group was 85.2%. The increase in hatching for an extracted mineral element composition group was 4.9%.

Thus, if the laying period for the primary breeders is 57 weeks, then 57 weeks×7 days per week equals 399 days. At 68,000 eggs per day, the total number of eggs for the 399 days is 27,132,000. Applying this number to the control group generates 21,786,996 chicks (i.e., 27,132,000 eggs× 80.3 hatching percentage). Applying this number to an extracted mineral element composition group generates 23,116,464 chicks (i.e., 27,132,100 eggs×85.2 hatching percentage). The increased difference in the number of chicks in the extracted mineral element composition group over the control group is 1,329,468 chicks (i.e., 23,116,464–21,786,996).

The extra earnings associated with the increase in the number of chicks generated by the extracted mineral element composition group was also calculated. The wholesale market value of a chick was calculated to be $0.37. At $0.37 per chick, the total wholesale market value of the increase of 1,329,468 chicks in the extracted mineral element composition group equals $491,903.16.

Example 2—Summary of Data from Chickens on Water or on Extracted Mineral Element Composition An extracted mineral element composition in water was provided to chickens and compared to water only (with no added extracted mineral element composition) provided to chickens and the growth performance of broilers and fryers and effects on hatching efficiency of primary breeders was examined. The study on broilers and fryers was carried out to conform to field conditions for 42 days. Similarly, primary breeders were used to evaluate an extracted mineral element composition in water for efficiency on percent hatching of eggs. Results after 42 days indicated that the broilers and fryers in the group receiving an extracted mineral element composition in water were significantly heavier than the water only group. In the primary breeder study, pullets receiving an extracted mineral element composition in water had significantly higher hatching rates than the control group through 75 weeks of age.

Figure 1A:
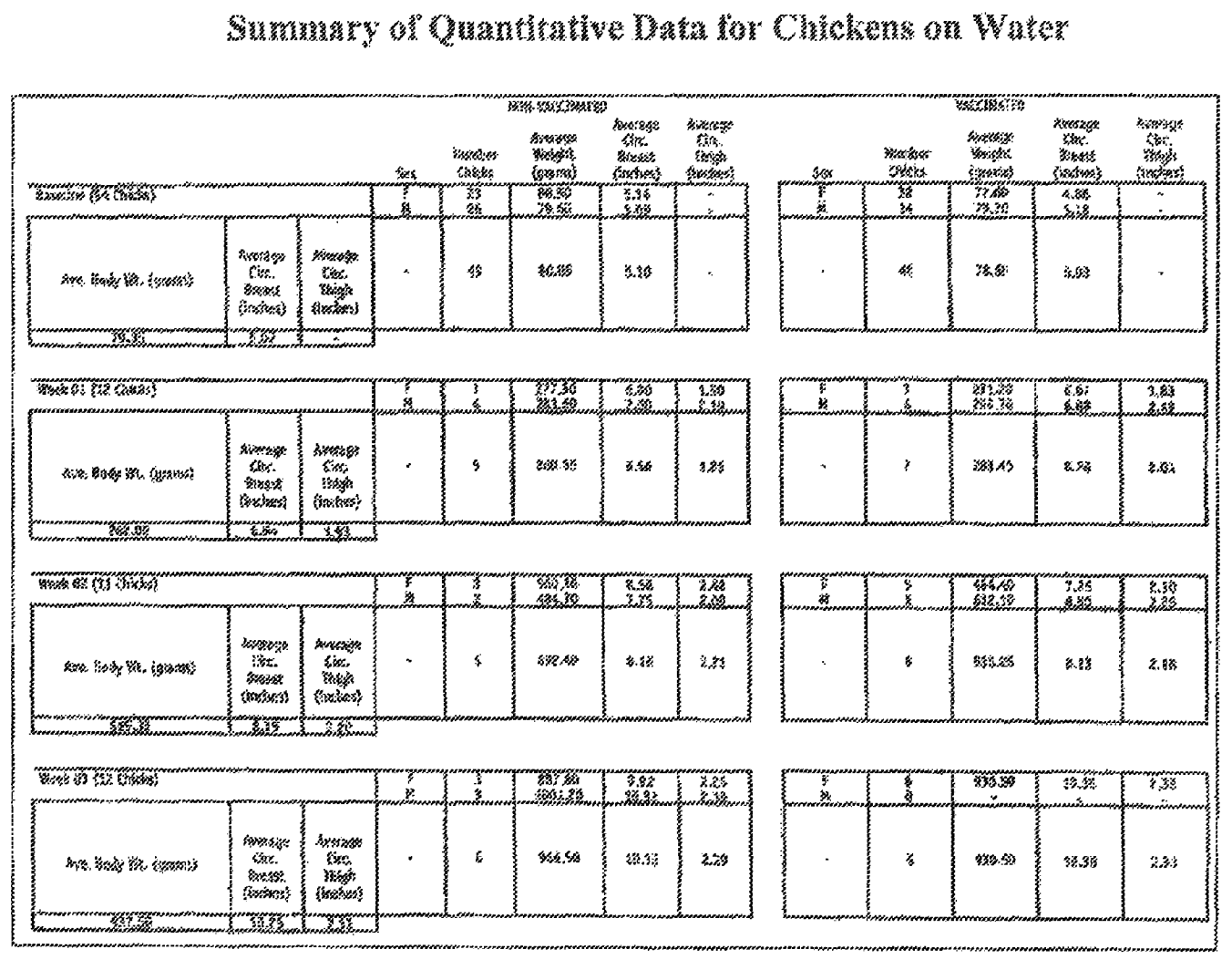
Figure 1B:
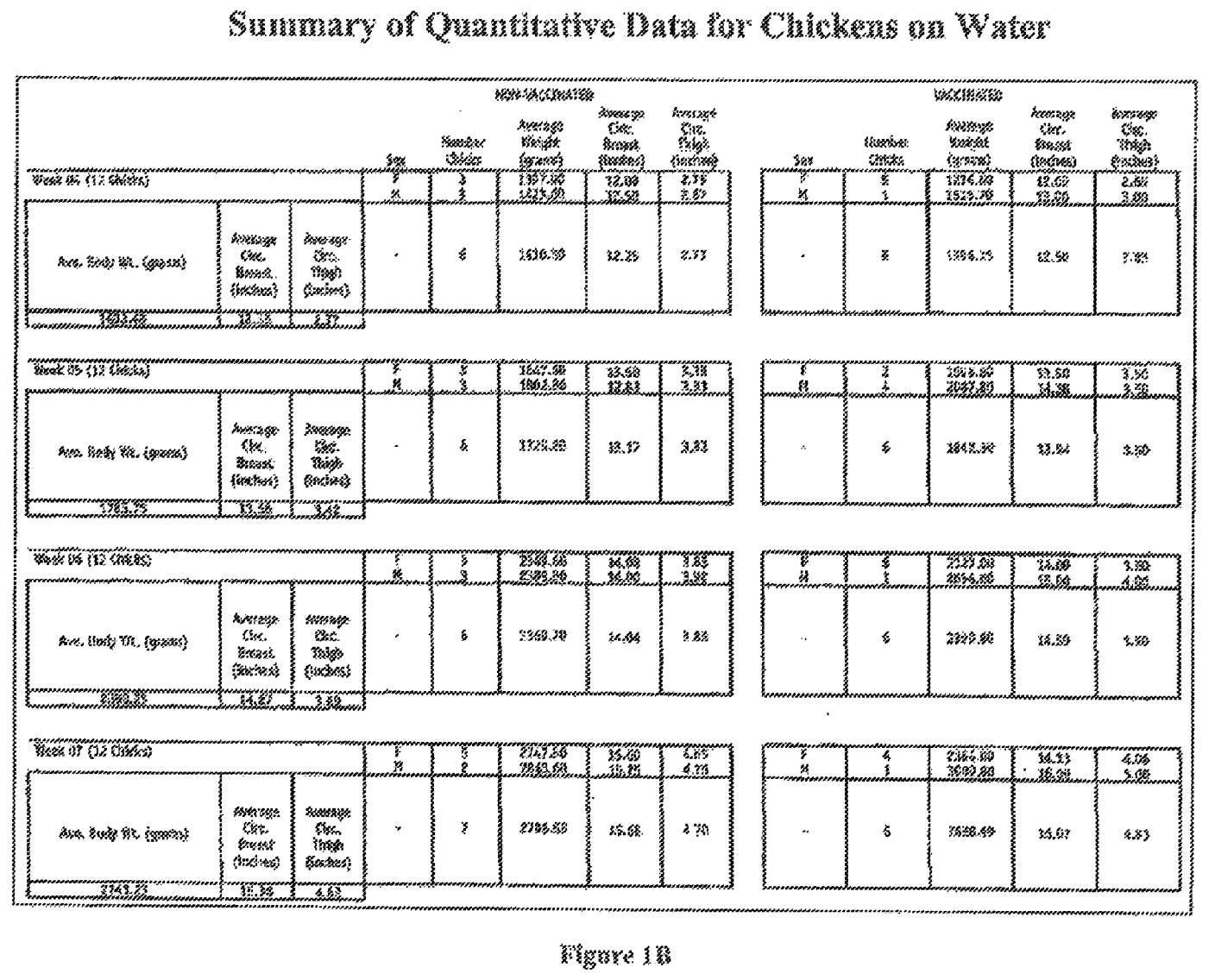
Figure 1D:
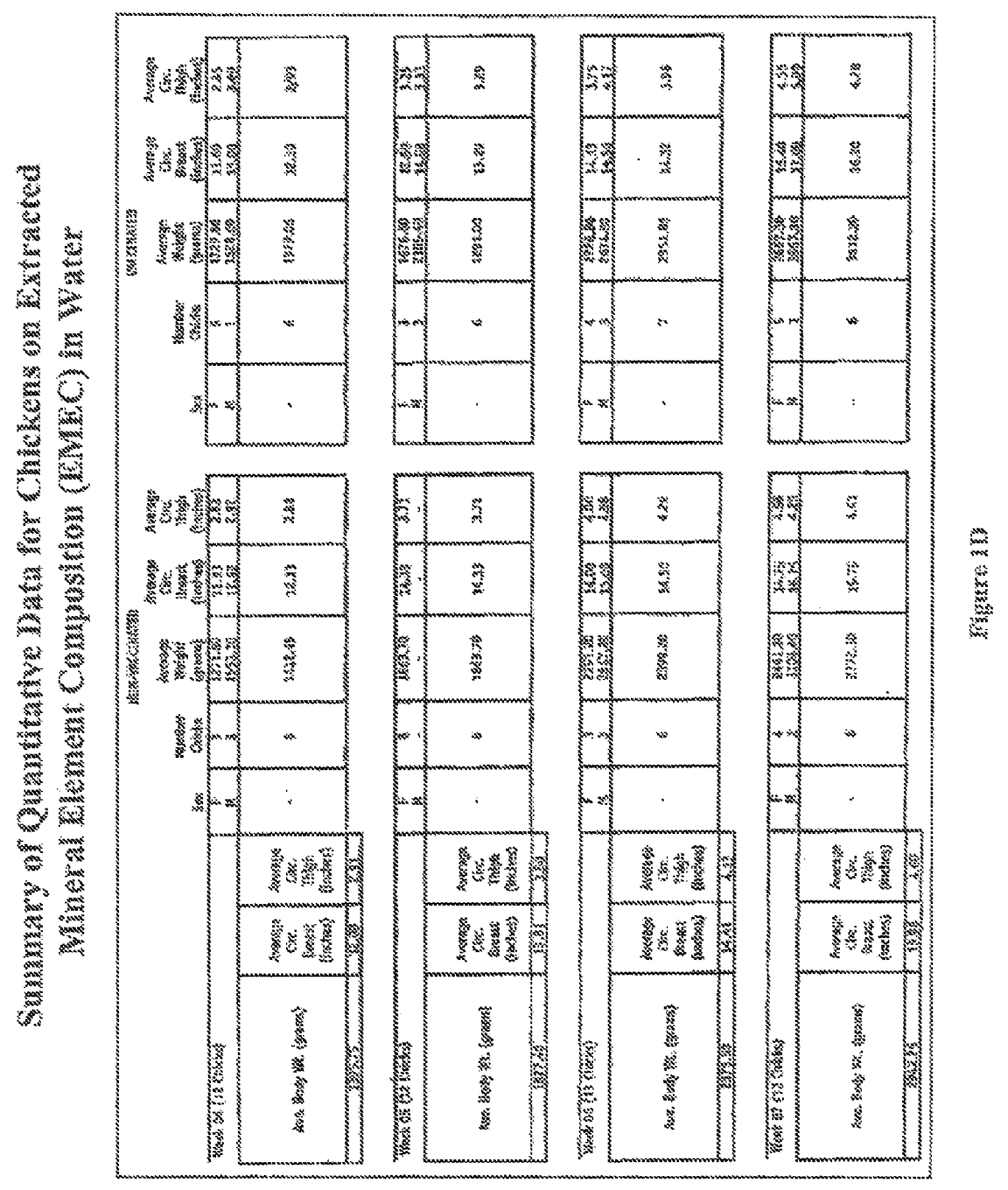

Quantitative data for vaccinated and non-vaccinated chickens was compiled across several weeks. FIGS. 1A-1D show quantitative data for vaccinated and non-vaccinated chickens across several weeks. FIG. 1A (baseline through week 3) and FIG. 1B (weeks 4-7) show data from chickens on water. FIG. 1C (baseline through week 3) and FIG. 1D (weeks 4-7) show data from chickens on extracted mineral element composition in water.

Regarding the average body weight of chickens on water or on extracted mineral element composition added to the water, the body weights of chickens in each group increased from baseline through seven weeks. Chickens receiving an extracted mineral element composition in water increased more in weight during weeks 5 and 7 than chickens receiving water only (FIG. 2).

Figure 3:
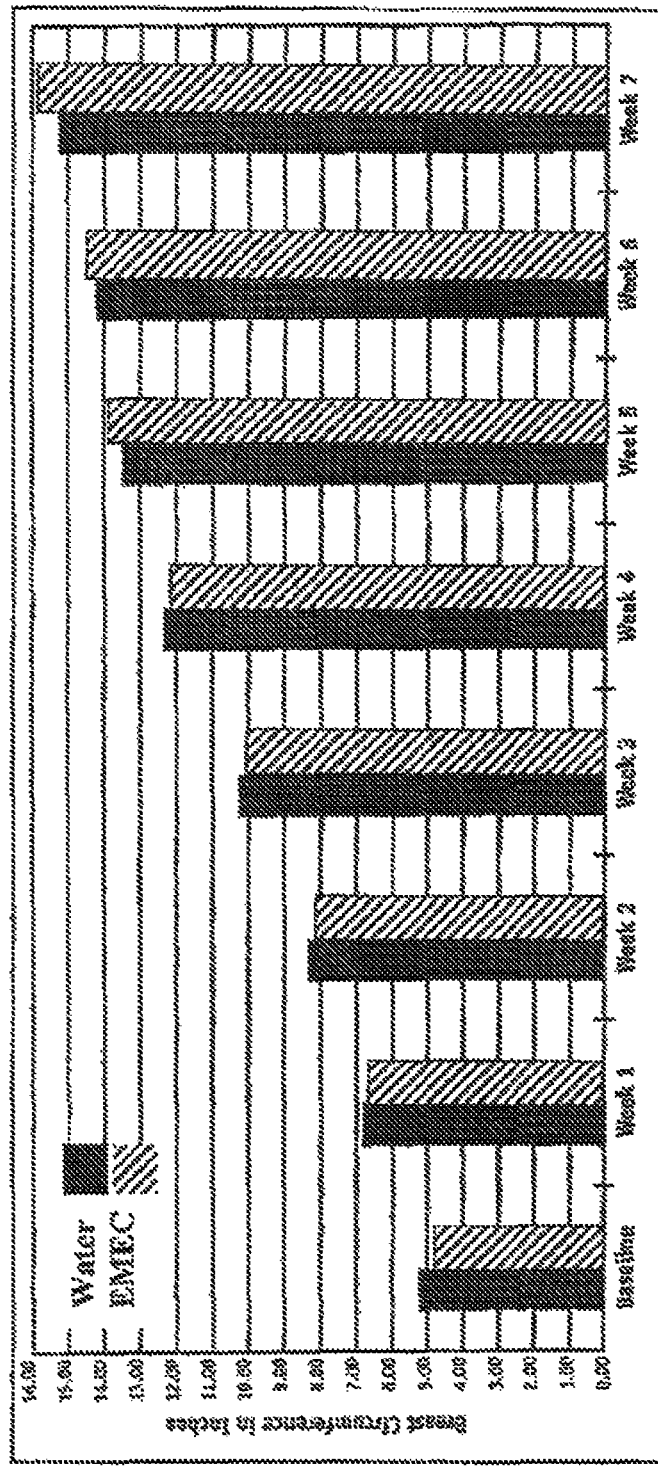
FIG. 3 shows the average breast circumference over several weeks for chickens on water and for chickens on extracted mineral element composition in water.

Regarding average breast circumference of chickens on water or on extracted mineral element composition in water, breast circumference of chickens in each group increased from baseline through seven weeks. The breast circumference of chickens receiving an extracted mineral element composition in water increased more during weeks 1, 5, 6, and 7 than those of chickens receiving water only (FIG. 3).

Figure 4:
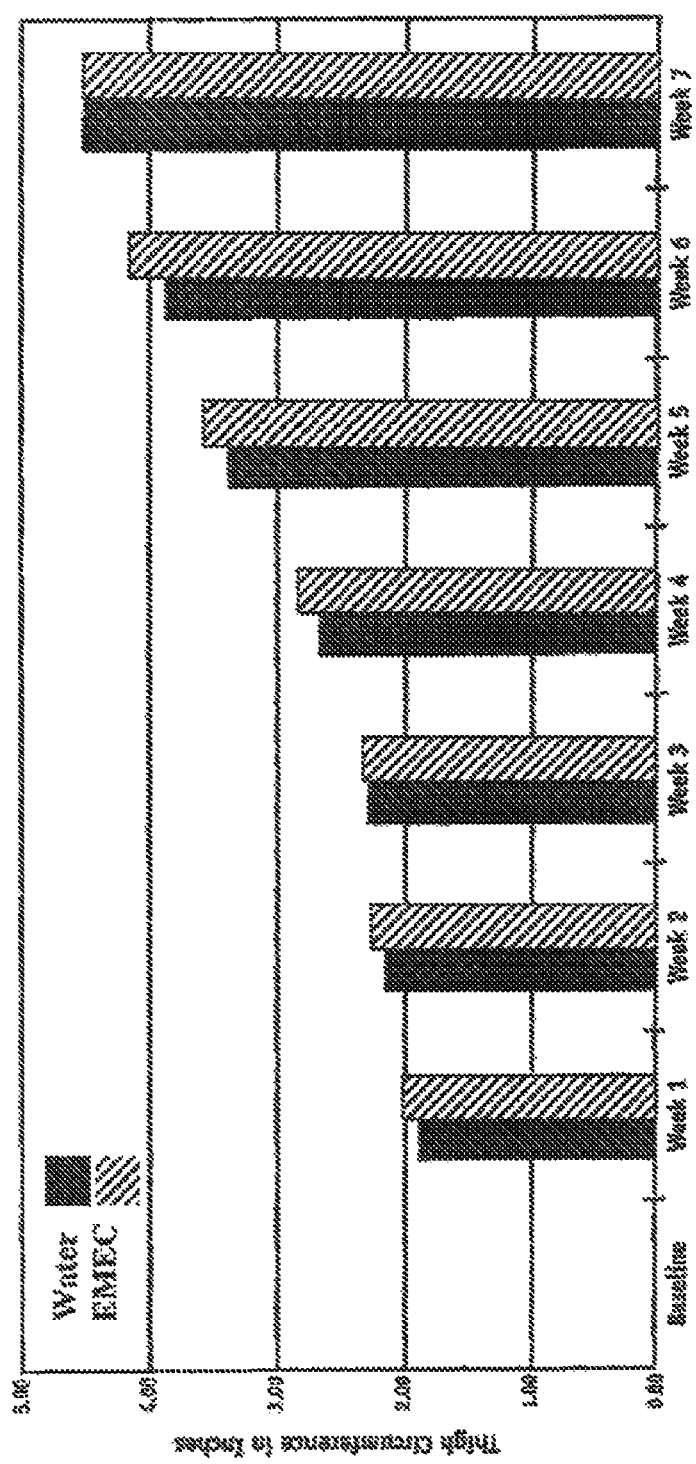
FIG. 4 shows the average thigh circumference over several weeks for chickens on water and for chickens on extracted mineral element composition in water.

Regarding average thigh circumference of chickens on water or an extracted mineral element composition in water, thigh circumferences of chickens in each group increased from baseline through seven weeks. Thighs of chickens receiving an extracted mineral element composition in water increased more in circumference during weeks 2, 3, 4, 5 and 6 than those of chickens receiving water only (FIG. 4).

Figure 5:
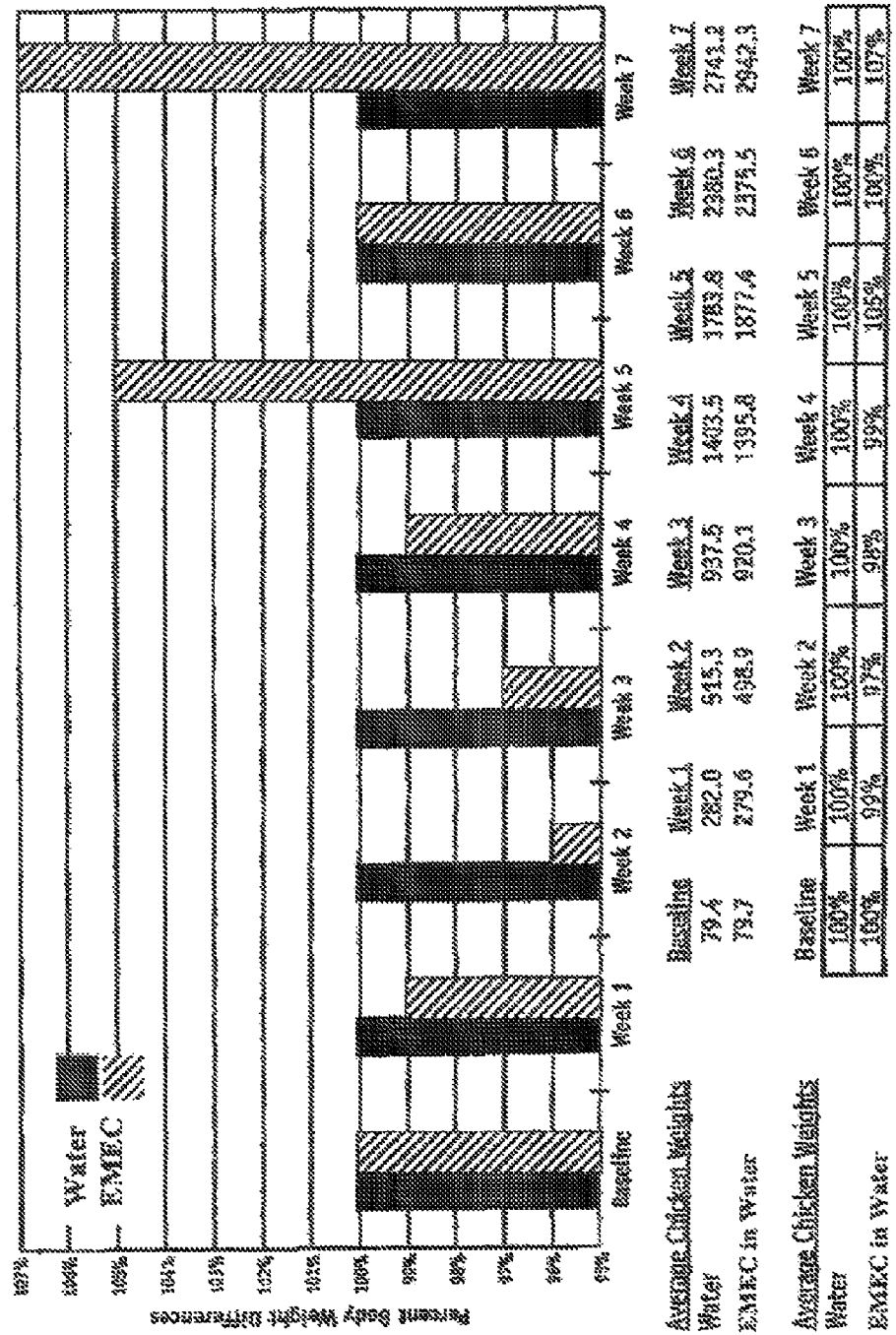
FIG. 5 shows the comparison of percent differences in the body weights over several weeks for chickens on water and for chickens on extracted mineral element composition in water.

Regarding the comparison of percent difference in body weight of chicken on water or on an extracted mineral element composition in water, increases in body weight were an average of 4% greater for chickens on an extracted mineral element composition in water during weeks 5, 6, and 7 (FIG. 5).

Figure 6:
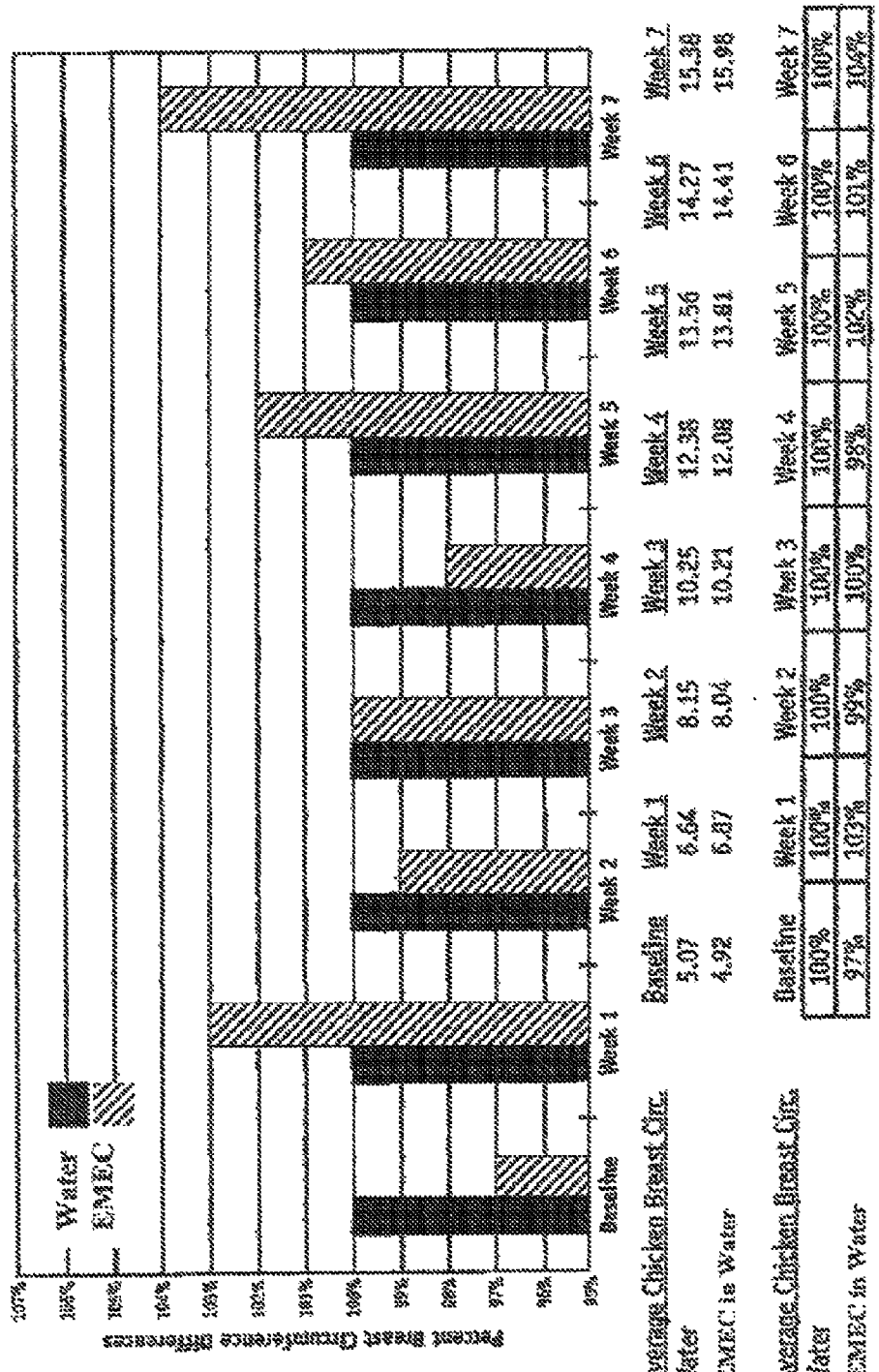
FIG. 6 shows the comparison of percent differences in the breast circumferences over several weeks for chickens on water and for chickens on extracted mineral element composition in water.

Regarding the comparison of percent difference in breast circumference of chickens on water or on an extracted mineral element composition in water, increases in breast circumference were 1-4% greater for chickens on an extracted mineral element composition in water during weeks 5, 6, and 7 (FIG. 6).

Figure 7:
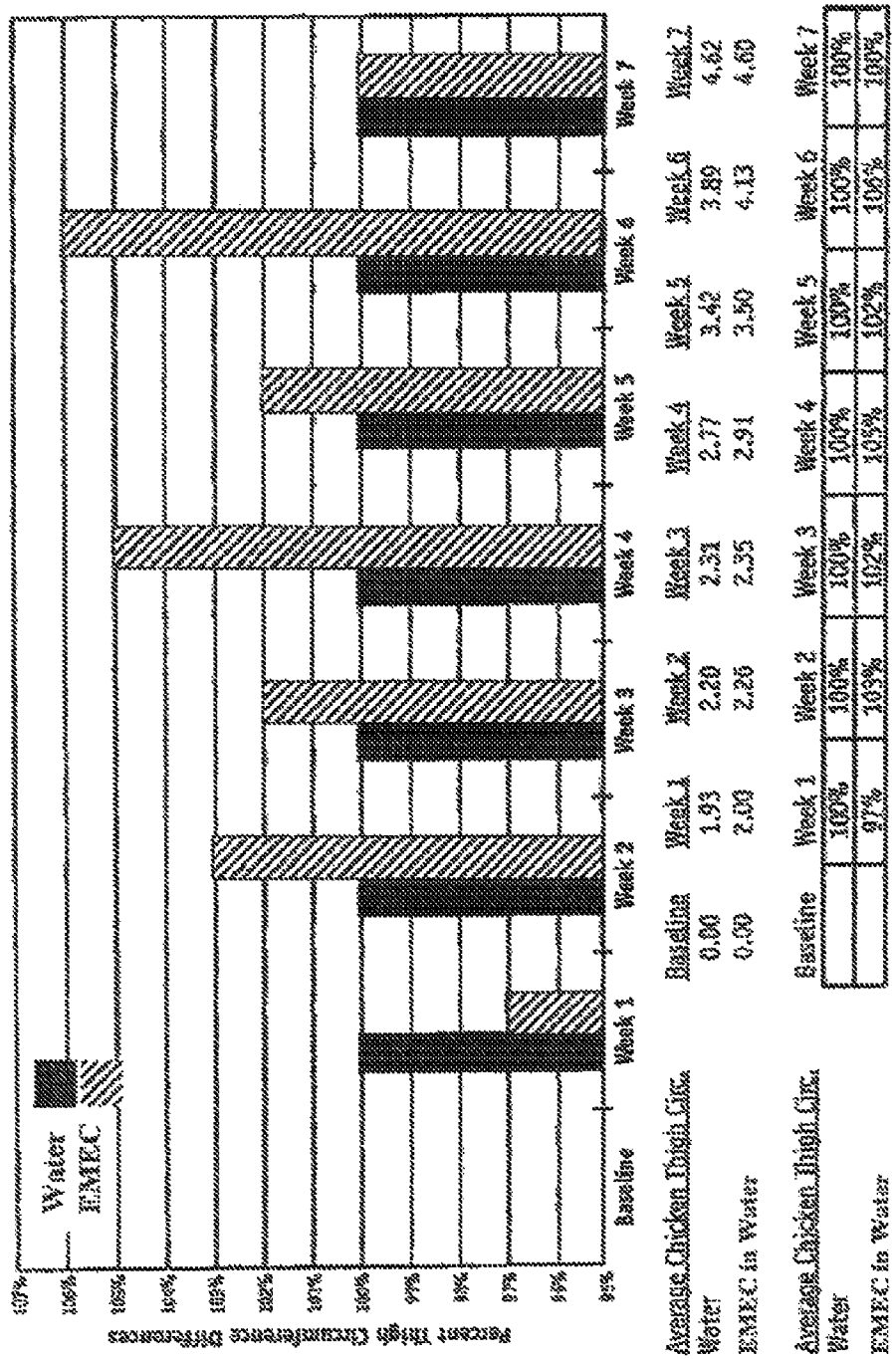
FIG. 7 shows the comparison of percent differences in the thigh circumferences over several weeks for chickens on water and for chickens on extracted mineral element composition in water.

Regarding comparison of percent difference in thigh circumference of chickens on water or on an extracted mineral element composition in water, increases in thigh circumferences were 2-6% greater during weeks 2-6 for chickens on an extracted mineral element composition in water (FIG. 7).

Regarding the average dressed weights for chickens on water or on an extracted mineral element composition in water, increases in dressed body weights were 5.9%, 11.5%, and 14.3% greater during weeks 5, 6, and 7, respectively, for chickens on an extracted mineral element composition in water (FIG. 8).

Figure 9:
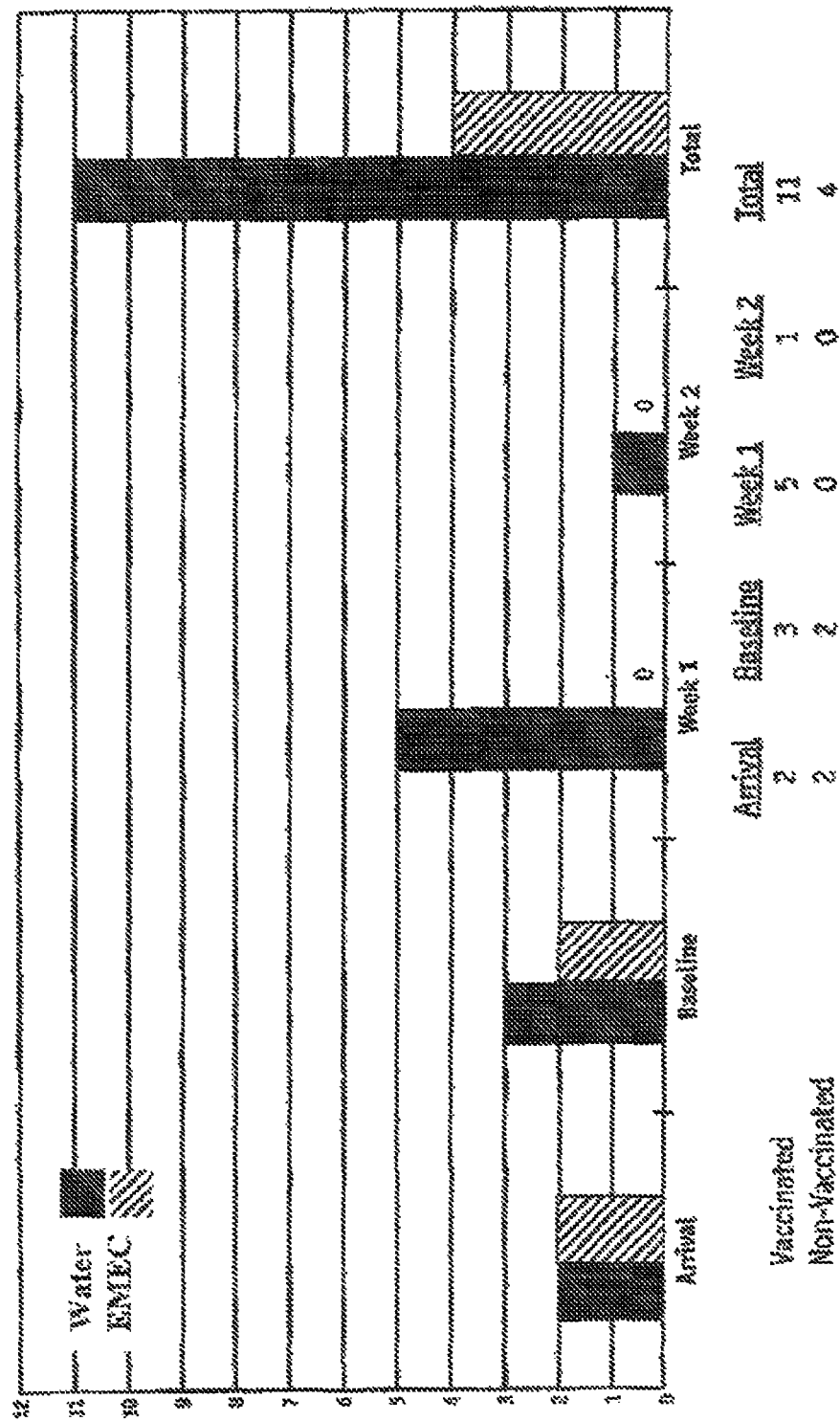
FIG. 9 shows the mortality rates of vaccinated and non-vaccinated chickens for chickens on water and for chickens on extracted mineral element composition in water.

Regarding mortality rate of vaccinated and non-vaccinated chickens, vaccinated chickens had a higher mortality rate. The first two weeks were the most critical for chicken survival (FIG. 9).

Figure 10:
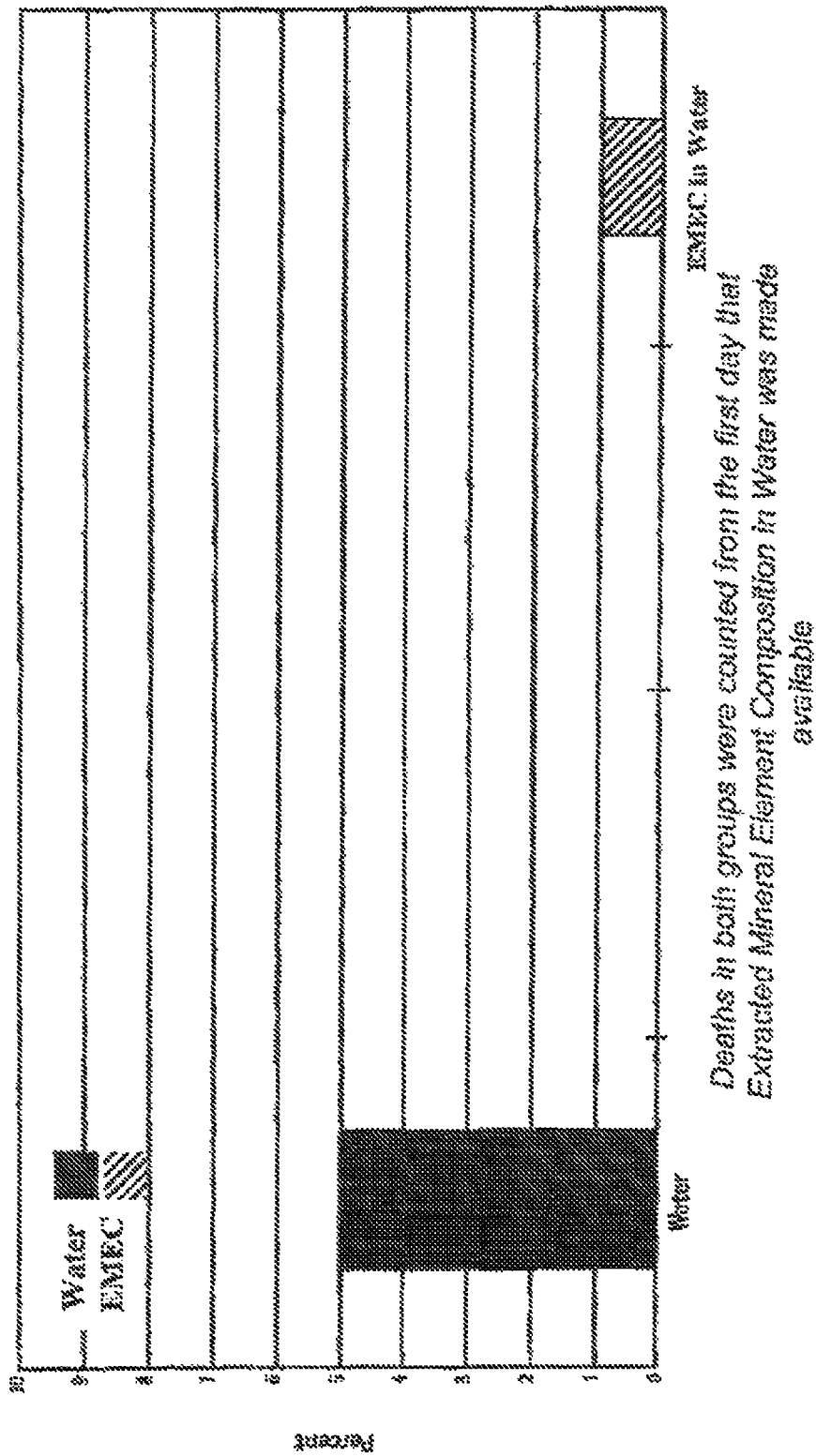
FIG. 10 shows the percent mortality rate of chickens on water and for chickens on extracted mineral element composition in water.

Regarding mortality rate of chickens on water or on an extracted mineral element composition in water, chickens on an extracted mineral element composition in water had reduced mortality rate (FIG. 10).

What is claimed:

1. A method of increasing hatch rate of eggs from laying poultry, breeder poultry, or meat production poultry, comprising, a) providing a composition to laying poultry, breeder poultry, or meat production poultry for a particular time period in the lifespan of the poultry, wherein the composition comprises an effective amount of an extracted mineral element composition prepared by a method consisting of:

one acid treatment step, a settling step, a separating step, a concentration step, and optionally, a drying step, wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;

wherein the settling step consists of allowing solids from the water-acid-soil slurry to settle;

wherein the separating step consists of separating the liquid of the water-acid-soil slurry from the settled solids wherein the settled solids comprise substantially all of the silicon and aluminum from the clay soil, mixture of clay soils, or a mixture of clay soils and leonardite;

wherein the concentrating step consists of concentrating the separated liquid to form a liquid extracted mineral element composition comprising calcium, chlorine, magnesium, manganese, phosphorous, potassium, silicon, and sodium, in a concentration from 0.0001% to 20.00% w/w;

wherein the optional drying step consists of drying the concentrated liquid to form a dry extracted mineral element composition; and wherein feeding laying poultry, breeder poultry, or meat production poultry the extracted mineral element composition increases egg hatch rate.

2. The method of claim 1, wherein the composition is provided in feed consumed by the poultry.

3. The method of claim 1, wherein the composition is provided in water consumed by the poultry.

4. The method of claim 1, wherein the composition is delivered to the poultry in capsules, powders, liquids, emulsions, oil-in-water, water-in-oil, suspensions, a poultry feed supplement, poultry feed, water compositions, or in liquid form.

5. The method of claim 1, wherein the extracted mineral element composition is in a liquid form.

6. The method of claim 1, wherein the extracted mineral element composition is in a dry form.

7. The method of claim 1, wherein the composition is provided to breeder chickens.

8. A method for increasing egg fertility of eggs from laying poultry, breeder poultry, or meat production poultry, comprising,
  a) providing a composition to laying poultry, breeder poultry, or meat production poultry for a particular time period in the lifespan of the poultry, wherein the composition comprises an effective amount of an extracted mineral element composition prepared by a method consisting of:
    one acid treatment step, a settling step, a separating step, a concentration step, and optionally, a drying step,
    wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;
    wherein the settling step consists of allowing solids from the water-acid-soil slurry to settle;
    wherein the separating step consists of separating the liquid of the water-acid-soil slurry from the settled solids wherein the settled solids comprise substantially all of the silicon and aluminum from the clay soil, mixture of clay soils, or a mixture of clay soils and leonardite;
    wherein the concentrating step consists of concentrating the separated liquid to form a liquid extracted mineral element composition comprising calcium, chlorine, magnesium, manganese, phosphorous, potassium, silicon, and sodium, in a concentration from 0.0001% to 20.00% w/w;
    wherein the optional drying step consists of drying the concentrated liquid to form a dry extracted mineral element composition; and
    wherein feeding laying poultry, breeder poultry, or meat production poultry the extracted mineral element composition increases egg fertility.

9. The method of claim 8, wherein the composition is provided in feed consumed by the poultry.

10. The method of claim 8, wherein the composition is provided in water consumed by the poultry.

11. The method of claim 8, wherein the composition is delivered to the poultry in capsules, powders, liquids, emulsions, oil-in-water, water-in-oil, suspensions, a poultry feed supplement, poultry feed, water compositions, or in liquid form.

12. The method of claim 8, wherein the extracted mineral element composition is in a liquid form.

13. The method of claim 8, wherein the extracted mineral element composition is in a dry form.

14. A method for improved egg production by laying poultry, breeder poultry, or meat production poultry, comprising,
  a) providing a composition to laying poultry, breeder poultry, or meat production poultry for a particular time period in the lifespan of the poultry, wherein the composition comprises an effective amount of an extracted mineral element composition prepared by a method consisting of:
    one acid treatment step, a settling step, a separating step, a concentration step, and optionally, a drying step,
    wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;
    wherein the settling step consists of allowing solids from the water-acid-soil slurry to settle;
    wherein the separating step consists of separating the liquid of the water-acid-soil slurry from the settled solids wherein the settled solids comprise substantially all of the silicon and aluminum from the clay soil, mixture of clay soils, or a mixture of clay soils and leonardite;
    wherein the concentrating step consists of concentrating the separated liquid to form a liquid extracted mineral element composition comprising calcium, chlorine, magnesium, manganese, phosphorous, potassium, silicon, and sodium, in a concentration from 0.0001% to 20.00% w/w;
    wherein the optional drying step consists of drying the concentrated liquid to form a dry extracted mineral element composition; and
    wherein feeding laying poultry, breeder poultry, or meat production poultry the extracted mineral element composition increases egg production and/or egg shell firmness.

15. The method of claim 14, wherein the composition is provided in feed consumed by the poultry.

16. The method of claim 14, wherein the composition is provided in water consumed by the poultry.

17. The method of claim 14, wherein the composition is delivered to the poultry in capsules, powders, liquids, emulsions, oil-in-water, water-in-oil, suspensions, a poultry feed supplement, poultry feed, water compositions, or in liquid form.

18. The method of claim 14, wherein the extracted mineral element composition is in a liquid form.

19. The method of claim 14, wherein the extracted mineral element composition is in a dry form.

20. The method of claim 14, wherein the composition is provided to laying hens.

* * * * *